(12) United States Patent
Mahal et al.

(10) Patent No.: US 10,610,454 B2
(45) Date of Patent: Apr. 7, 2020

(54) SYSTEM FOR DELIVERY AND CONTROL OF MEDICATIONS AND RELATED METHODS

(71) Applicant: Rajwant Singh Mahal, Fresno, CA (US)

(72) Inventors: Rajwant Singh Mahal, Fresno, CA (US); Michael Robert Grace, Jr., New Haven, CT (US)

(*) Notice: Subject to any disclaimer, the term of this patent is extended or adjusted under 35 U.S.C. 154(b) by 134 days.

(21) Appl. No.: 15/754,423

(22) PCT Filed: Aug. 25, 2016

(86) PCT No.: PCT/US2016/048563
§ 371 (c)(1),
(2) Date: Feb. 22, 2018

(87) PCT Pub. No.: WO2017/035308
PCT Pub. Date: Mar. 2, 2017

(65) Prior Publication Data
US 2018/0243170 A1    Aug. 30, 2018

Related U.S. Application Data

(60) Provisional application No. 62/338,754, filed on May 19, 2016, provisional application No. 62/209,690, filed on Aug. 25, 2015.

(51) Int. Cl.
*A61J 7/00* (2006.01)
*B65D 83/08* (2006.01)
(Continued)

(52) U.S. Cl.
CPC .............. *A61J 7/0084* (2013.01); *A61J 1/03* (2013.01); *A61J 7/0076* (2013.01); *A61J 7/04* (2013.01);
(Continued)

(58) Field of Classification Search
CPC ........ A61J 1/03; A61J 3/00; A61J 7/00; A61J 7/02; A61J 7/04; A61J 7/0076;
(Continued)

(56) References Cited

U.S. PATENT DOCUMENTS 2,587,928 A * 3/1952 Tuck .................. B65D 83/0472
221/25
2,771,214 A * 11/1956 Lefebvre ............ B65D 83/0472
221/25
(Continued)

FOREIGN PATENT DOCUMENTS

WO    WO 2004/028438 A2    4/2004

OTHER PUBLICATIONS

PCT International Search Report and Written Opinion for PCT/US2016/048563 dated Dec. 30, 2016.
(Continued)

*Primary Examiner* — Gene O Crawford
*Assistant Examiner* — Ayodeji T Ojofeitimi
(74) *Attorney, Agent, or Firm* — McCarter & English, LLP

(57) ABSTRACT

Systems/methods for delivery and control of medications for patient use and, more particularly, to dispenser-based systems that facilitate access to and use of individually packaged sets of medications (e.g., pills, tablets and the like), and associated control functionalities that monitor and communicate the status/inventory of medications associated with the dispenser-based system, are provided. Systems/methods that include indicia associated with the packaged sets of medications and for "reading" the indicia to monitor or determine the status or position of the packaged set of medications are also provided.

20 Claims, 20 Drawing Sheets

(51) Int. Cl.
*A61J 1/03* (2006.01)
*A61J 7/04* (2006.01)
*G16H 20/13* (2018.01)

(52) U.S. Cl.
CPC ......... *B65D 83/0894* (2013.01); *G16H 20/13* (2018.01); *A61J 2200/30* (2013.01); *A61J 2205/10* (2013.01)

(58) Field of Classification Search
CPC .... A61J 7/0084; A61J 7/0409; A61J 2205/10; A61J 2205/30; G06F 19/00
See application file for complete search history.

(56) References Cited

U.S. PATENT DOCUMENTS

| | | | | |
|---|---|---|---|---|
| 2,889,958 | A * | 6/1959 | Svensson | B65D 75/42 221/25 |
| 2,984,397 | A * | 5/1961 | Gillam | B65D 83/0472 225/49 |
| 3,001,643 | A * | 9/1961 | O'Meara | B65D 83/0472 206/526 |
| 3,115,989 | A * | 12/1963 | Strang | B65D 83/0472 221/25 |
| 3,362,578 | A * | 1/1968 | Spencer | B65D 83/0472 221/25 |
| 5,957,358 | A * | 9/1999 | Getz | B65D 83/0472 206/820 |
| 7,963,201 | B2 * | 6/2011 | Willoughby | A61J 7/0084 117/106 |
| 8,086,350 | B2 | 12/2011 | Timmermans et al. | |
| 8,196,774 | B1 * | 6/2012 | Clarke | A61J 7/0409 221/13 |
| 8,757,435 | B2 | 6/2014 | Van Oort et al. | |
| 2003/0075561 | A1 * | 4/2003 | Pieri | B65D 75/527 222/94 |
| 2004/0065670 | A1 * | 4/2004 | Morgan | A47L 15/4472 221/33 |
| 2004/0158349 | A1 | 8/2004 | Bonney et al. | |
| 2004/0158350 | A1 * | 8/2004 | Ostergaard | A61J 7/0481 700/231 |
| 2005/0049747 | A1 | 3/2005 | Willoughby et al. | |
| 2005/0061825 | A1 * | 3/2005 | Willoughby | B65D 75/42 221/2 |
| 2007/0095850 | A1 * | 5/2007 | Meyer | A61J 1/035 221/2 |
| 2008/0078767 | A1 * | 4/2008 | Gardner | B65D 75/42 220/507 |
| 2008/0093365 | A1 | 4/2008 | Catron | |
| 2008/0290106 | A1 * | 11/2008 | van der Klaauw | A61J 7/0076 221/1 |
| 2009/0277918 | A1 * | 11/2009 | Dixon | B65D 83/0472 221/1 |
| 2010/0038374 | A1 * | 2/2010 | Campi | A61F 13/0276 221/46 |
| 2010/0114367 | A1 * | 5/2010 | Barrett | G06F 19/3456 700/236 |
| 2011/0048993 | A1 * | 3/2011 | Gretzinger | B65D 5/0227 206/391 |
| 2011/0079606 | A1 * | 4/2011 | Weston | B65D 5/10 221/282 |
| 2011/0100863 | A1 * | 5/2011 | Luciano | A61J 1/03 206/534 |
| 2011/0208348 | A1 | 8/2011 | Bogue | |
| 2012/0145739 | A1 * | 6/2012 | Doyle | A61J 1/035 221/89 |
| 2013/0066463 | A1 * | 3/2013 | Luoma | A61J 1/035 700/232 |
| 2013/0175286 | A1 * | 7/2013 | Barrett | A61J 1/035 221/1 |
| 2013/0256392 | A1 * | 10/2013 | Kohler | B65D 5/72 229/117.12 |
| 2014/0005826 | A1 | 1/2014 | Apell et al. | |
| 2016/0106625 | A1 * | 4/2016 | Dunleavy | A61J 7/0084 206/534 |
| 2017/0247172 | A1 * | 8/2017 | Edwards | B65D 65/46 |
| 2018/0303719 | A1 * | 10/2018 | DeLury | A61J 7/0084 |

OTHER PUBLICATIONS

U.S. Appl. No. 62/209,690, filed Aug. 25, 2015.
PCT/US2016/048563, Aug. 25, 2015, WO/2017035308.
U.S. Appl. No. 62/338,754, filed May 19, 2016.

* cited by examiner

FIG. 12A

Settings

The patient's medication schedule will consist of a list of four times for each dose, a number identifying the number of doses/packs for the prescription ("ND"), and a set minimum value ("m"). The four times are the "Medication Time" (when the dose should be taken), the "Earliest Medication Time" (the earliest time before the Medication Time -- we will assume the dose was consumed and not taken in preparation to consume later), the "Notification Start Time" (when notifications will begin for that dose), the "Notification End Time" (when notifications will cease for that dose). Below is an example of this list for just a few doses. A real schedule would cover 2-4 weeks of doses.

| Medication Time | Earliest Medication Time | Notification Start Time | Notification End Time | Number of Doses/Packs ("N") |
|---|---|---|---|---|
| Monday 8:00AM | Monday 5:30AM | Monday 6:30AM | Monday 11:00AM | 30 |
| Tuesday 6:00PM | Tuesday 2:05PM | Tuesday 6:30PM | Tuesday 9:00PM | Set Minimum Value ("v") |
| Wednesday 9:30AM | Wednesday 7:00AM | Wednesday 9:30AM | Wednesday 12:30AM | 3 |
| Wednesday 6:00PM | Wednesday 3:30PM | Wednesday 6:30PM | Wednesday 9:00PM | |

Users will also be able to set the notification frequency, medium, and who is notified. (See communication section for methods that the patient can use to update these settings).

Initialization

In the process of inserting the small box into the big box a reset button is triggered. The system then calculates the number of doses in the small box. The measured number of doses from initialization is stored as the variable T.

System checks this number of doses (T) against the last stored value for the number of doses in the strip ("M"). If this is the first time the device has been loaded, 'M' is preset as 0. There are two possible results.

1. If T is less than or equal to 'M'.
   The system assumes it is the same small box.

2. If T is greater than 'M'.
   The system assumes that a new small box has been inserted.

The system retrieves the latest updated settings. The expected number of doses in the system, 'X', is increased by adding 'N' from the updated settings. If this was the first time the device was loaded, 'X' is preset as 'v'.

Continued to Next Page

Hard reset

If a hard reset button is pressed, the system will measure the number of doses in the strip and initialize that value as 'X' (the expected number of doses in the system) and retrieve the latest updated settings.

Continued to Next Page

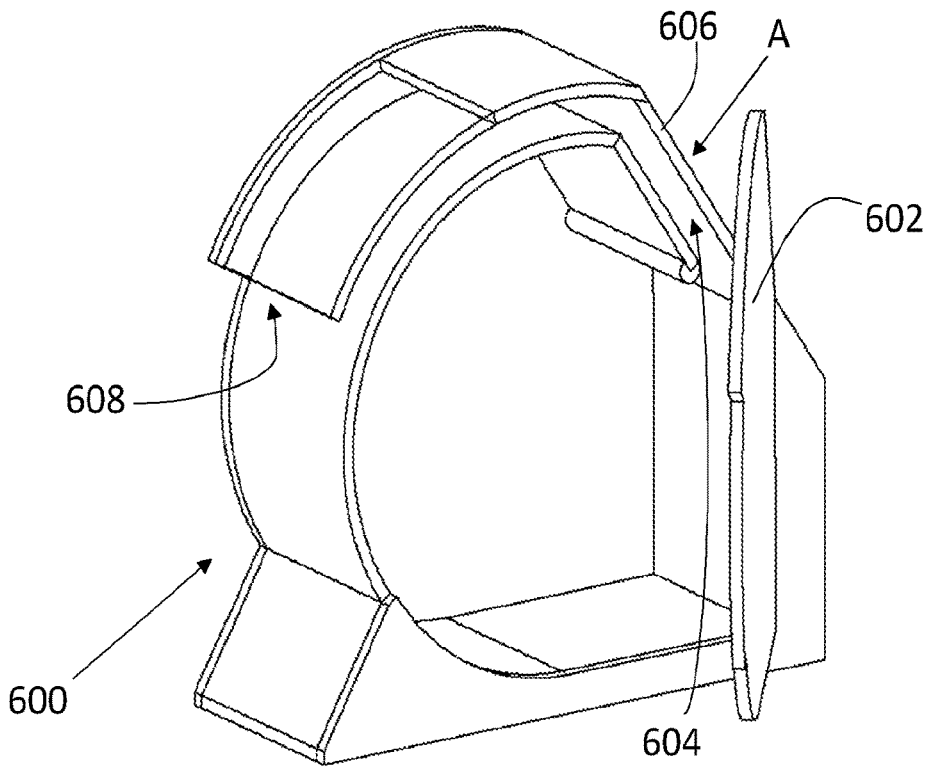
Fig. 16
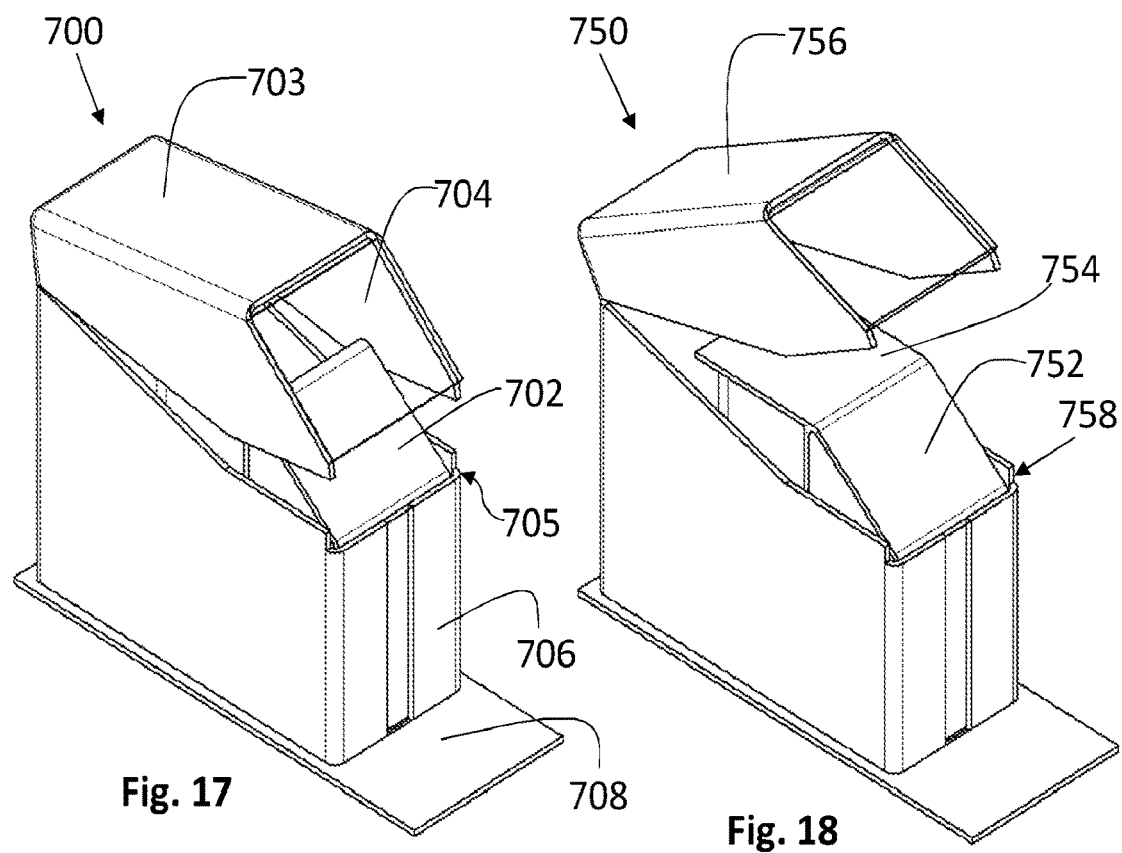
Fig. 17
Fig. 18

SYSTEM FOR DELIVERY AND CONTROL OF MEDICATIONS AND RELATED METHODS

BACKGROUND

1. Technical Field

The present disclosure is directed to systems/methods for delivery and control of medications for patient use and other purposes (e.g., clinical trials) and, more particularly, to dispenser-based systems that facilitate access to and use of individually packaged sets of medications (e.g., pills, tablets and the like), and associated control functionalities that monitor and communicate the status/inventory of medications associated with the dispenser-based system.

2. Background Art

The prior art includes well established forms of medication packaging known as unit-and/or multi-dose strip medication packaging. The noted approach to medication packaging permits individualized/customized sets of medications to be combined and delivered to patients, thereby enhancing the efficiency and reliability of medication use, e.g., for patients who are required to ingest a plurality of medications on a routine basis.

Despite the development and adoption of unit-/multi-dose modalities for packaging of medications for use by patients, a need remains for improved medication delivery systems that facilitate, inter alia, (i) storage of and access to individual medication packages, (ii) automatic monitoring and/or transmission of medication inventory information, (iii) reminders/cues for improved medication adherence, and (iv) child-resistant storage of packaged medications.

More particularly, it is noted that prior art motorized dispensing systems are dependent on the motorized mechanism to monitor dispensing status. This dependence on the motorized mechanism significantly limits the flexibility of the monitoring functionality and restricts the ability of a system user to access medications on an immediate and/or intermittent basis, i.e., independent of the scheduled dispensing schedule, without a potentially cumbersome and multi-step system interaction. Indeed, prior art dispensing systems are generally rigid and specific in the requirements imposed upon users to access medication doses, often requiring careful alignment of the dispensing strip with the dispensing apparatus to ensure proper monitoring of the dosing status, etc. Prior art systems do not permit the user to see and/or access medication doses on an as-desired basis. Still further, prior art systems generally impose a frustrating time delay from the point that the user seeks to separate a medication dose from the system and the time when such medication dose is released to the user, and require the user to affirmatively signal that the user has completed his/her interaction with the dosing system before monitoring functionality associated with the prior art dosing system is prompted to perform/update its dispensing status.

These and other limitations and shortcomings of the prior art are advantageously addressed and overcome by the disclosed systems and methods.

SUMMARY

The disclosed systems and methods generally utilize packaging strips that include a plurality of individually sealed pouches, each pouch containing single or multiple medications.

Each pouch generally includes printed indicia related to the pouch content and/or patient. For example, the printed indicia may include a listing of the medications included in the sealed pouch, potency of the medications, manufacturer of the medications, patient name, patient reference information, date of packaging, expiration date(s) for medications, prescribing physician information, date and time to consume dose, prescribing pharmacy information, and the like. The pouch may include at least one transparent face, e.g., a transparent face and a non-transparent face, or two opposed transparent faces, or may be defined by opposing non-transparent faces, as is known in the art.

According to the present disclosure, each sealed pouch in the strip encloses an individual dose that is generally customized for a particular patient. The systems and methods of the present disclosure advantageously permit the number of pouches/doses that remain in a strip to be automatically monitored/logged. This data can then be used by the system in combination with the patient dose schedule and other patient information to provide appropriate reminders/cues to the patient to assist with medication adherence. Data collected by the system may also be shared with other parties to assist in the patient's medication adherence.

In exemplary embodiments of the present disclosure, the packs may have/contain, inter alia, images, text, symbols, print, barcodes, 2D barcodes, RFID tags, metallic tags/ink, electromagnetic tags/ink, smart devices, electrical circuitry, or other indicia/tags that cooperate with strategically positioned electrical devices (e.g., camera, barcode scanners/readers, CCD, QR code reader/scanner, RFID reader/scanner, pen reader, 2D scanner/reader, NFC device, electromagnetic transmitter/receiver, MCU, ASIC, switches, electrical contacts, light sensors etc.) external to the strip. This cooperation includes, inter alia, reading, scanning, capturing, measuring, or sensing the indicia by means of, inter alia, electromagnetic waves, magnetic fields, electrical current, light, sound, infrared, material compression, material expansion, movement, mechanical sensing. The term "reading" shall be used herein to refer to any of these forms/methods of cooperation. In general, the cooperation of the electrical device with the indicia on the strip may relay information about the position, status, and/or movement of the strip, which may then be used to approximate/determine the number of packs/doses that remain connected to the strip. The cooperation may also relay information that may be used by the system to approximate whether the system was loaded correctly, if a person is interacting/engaging with the system, and if the location of the strip/packs is not within the bounds measurable by the system (i.e., if the strip physically extends to/beyond the physical bounds where the system is expected to reliably approximate the number of packs that remain connected to the strip).

Furthermore, embodiments of the present disclosure that utilize indicia/tags to approximate/determine the number of packs/doses remaining in the strip may benefit from cooperation with systems that can determine the displacement, and/or position, and/or status of the strip and its contents without the use indicia/tags. These hybrid embodiments allow for a system that can leverage benefits from each technique, some of which will be discussed herein.

The present disclosure thus provides highly advantageous dosage logging systems/methods that may be implemented and/or employed with existing and future strip packaging techniques, i.e., individually sealed pouches, containers or other packaging modalities that deliver their contents in a strip. The present disclosure also provides advantageous systems/methods for monitoring the position and/or status of strip packages that are effective without any electrically driven moving parts to dispense the strip. Although the disclosed strip dispensing system could be motorized and still reliably monitor the status of a strip, the systems and methods of the present disclosure do not require motors associated with a motorized dispenser to monitor the strip status.

Furthermore, the disclosed systems and methods advantageously allow the user immediate and instant access to any of their doses. The user's access to particular dose(s) is not restricted to particular times and the user is not required to engage in a cumbersome process, e.g., a process that may involve pressing a series of buttons and responding to a series of prompts to access their doses.

Indeed, the disclosed systems and methods provide a stronger marriage between automation and user freedom and flexibility in interacting with his/her medication doses. The disclosed system can effectively monitor the status of the strip while requiring little to no extra effort on the part of the user apart from the user separating his/her dose(s) from the strip. The user experiences beneficial freedom and flexibility in choosing when to take each individual dose out of the system; the user is not confined to removing the dose from the system in a cumbersome, specific and/or meticulous manner.

With exemplary embodiments of the disclosed system/method, precise and meticulous positioning of the leading edge of the strip is not critical to the system operation and dosage monitoring functionality. Indeed, in embodiments of the disclosed system/method the leading edge of the strip can span an area up to or greater than a single pack and the embodiments can still automatically determine the status of the strip. Furthermore, users of the disclosed system/method are not required to notify the system that the user has accessed/retrieved the desired medication doses (e.g. by pressing buttons). Rather, exemplary embodiments of the disclosed system are able to automatically approximate/determine when the user is done using the system and automatically act from there.

Due to physical design and algorithms associated with exemplary embodiments of the disclosed system/method, the present disclosure largely allows any portion of the face of the strip with the barcodes to be in the scanning region and the system will still be able to scan the barcode(s) on the pack(s) and determine which position of the strip is in the scanning region. Thus the user may leave the leading edge of the strip over an area that extends from within the scanning region to some distance beyond the outer border of the scanning region (i.e. the border furthest along the expected travel path of the strip), without negatively impacting the functionalities of the disclosed system.

The strip of the present disclosure may be exposed outside of the container without negatively impacting the functionalities of the system (e.g., the system can still determine the status of the strip) based, in whole or in part, on the use of sensors in the front of the container that detect for the additional packs along with the use of algorithms that connect information from these sensor(s) with information from the scanner(s). This feature, in combination with the system's scanning capability, allows the user to leave the leading edge of the strip over an even greater range of area. This feature, specifically, extends the area beyond the outer border of the scanning region where the leading edge of the strip may be positioned. Of note, the disclosed system generally includes sensor(s) that can determine if the strip extends beyond the range of area permitted according to the present disclosure, and generates a notification if the leading edge is outside such permitted range of locations.

Through the use of strategically placed IR/distance/proximity/motion sensors and software delays, the disclosed system is able to automatically approximate whether the system is in use or not. This is important not only for power saving but also because the system can automatically approximate when the user is done using the system and then automatically begin to log the status of the strip and automatically act on that information without needing the user to take an additional step to notify the system that they are done using the system (e.g. by pushing a button).

The automation created by the IR/distance/proximity/motion sensors and software delays that approximate when the user is done using the system greatly enhance the design and operation of exemplary embodiments of the present disclosure as discussed herein. And the leeway/flexibility for the position of the leading edge of the strip, (e.g., based on the disclosed barcode functionality in combination with the disclosed sensor functionality in the front of the dispenser that detect for the additional packs) greatly enhances the benefits of the disclosed system/method from a user perspective.

Additional features, functions, and benefits of the disclosed systems and methods will be apparent from the detailed description which follows.

BRIEF DESCRIPTION OF THE FIGURES

To assist those of skill in the art in making and using the systems and methods disclosed herein, reference is made to the accompanying figures, wherein:

FIGS. 12A and 12B depict a "decision tree" flowchart, wherein the decision tree flow chart spans over two pages that connect to each other based on the bridging lines;

FIG. 16 depicts an alternate embodiment of the big box that tracks the dispensing of packets by a indicia-reading capabilities, according to the present disclosure;

FIG. 17 depicts a perspective view of an alternate embodiment of a partially opened big box that provides indicia-reading capabilities of an ascending strip, according to the present disclosure;

FIG. 18 depicts a perspective view of an alternate embodiment of a partially opened big box that provides indicia-reading capabilities of an ascending strip, according to the present disclosure;

DESCRIPTION OF EXEMPLARY EMBODIMENT(S)

As noted above, the present disclosure is directed to systems/methods for delivery and control of medications for patient use. The disclosed dispenser-based systems advantageously facilitate access to and use of individually packaged medications (e.g., pills, tablets and the like). Moreover, the disclosed systems and methods include one or more functionalities that automatically monitor the status/inventory of medications associated with the dispenser-based system. In exemplary implementations of the disclosed systems/methods, the status/inventory of medications may be communicated via cues (visual and/or audible and/or physical) from the system or an external electronic device, e.g., a smart phone or other processing unit, to alert a patient, health care provider, or other third party (e.g., parent, spouse, etc.) as to the status of medication inventory and/or use.

Strip Packaging Modification

In a first exemplary embodiment of the disclosed system/method, the strip is associated with a dispensing unit/housing that includes functionality adapted to directly measure the number of pouches associated with the strip/packaging via a cooperative modification to the strip/packaging itself using electrical circuitry as tags/indicia on each pouch/pack. As pouches are torn off of the strip, the disclosed system measures/records a change in the cooperative modification and therefore a change in the number of doses remaining.

According to exemplary embodiments of the present disclosure, two electrically conductive materials (e.g. solder, copper tape, conductive ink, metal wire) are positioned parallel (or in an otherwise spaced arrangement) relative to each other, e.g., along the sides of the strips. The spaced conductive materials may be referred to as "rails". On each pouch, an electrically resistive material (e.g., a resistor, carbon resistor, resistive ink, carbon tape, carbon ink) is provided that connects the two spaced rails. The electrically resistive/connective material may be referred to as a "cross-tie".

Figure 1:
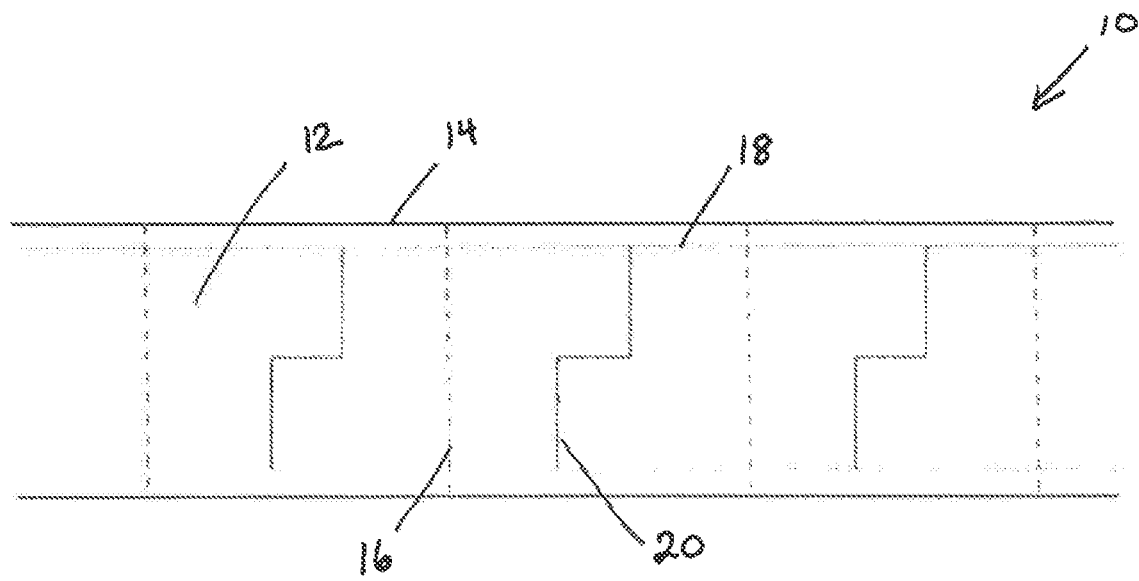
FIG. 1 depicts a small piece of strip packaging according to the present disclosure.

FIG. 1 depicts a small piece of strip packaging 10 according to an exemplary implementation of the present disclosure. The outer-most lines 14 represent the outside edges of the strip packaging 10 and the lines 16 that are substantially perpendicular to the outside edges represent separations between the individually sealed medication-containing pouches 12 defined by such separations. Each separation 16 is generally sealed plastic that is either perforated or has a cut at one or both sides so that the pouches can be easily separated from each other without having to expose their contents. The lines positioned inward of and parallel to the edges represent conductive rails 18 that run along the length of the strip packaging 10. The spaced lines that connect the conductive rails represents the resistive cross-ties 20 that extend over each pouch 12. Although the resistive cross-ties 20 are shown with an intermediate jog, the present disclosure is not limited by or to the exemplary circuitry embodiments depicted below. A three dimensional (3D) model of an exemplary packaging strip 10 with conductive circuitry according to the present disclosure is illustrated in FIG. 2.

Figure 2:
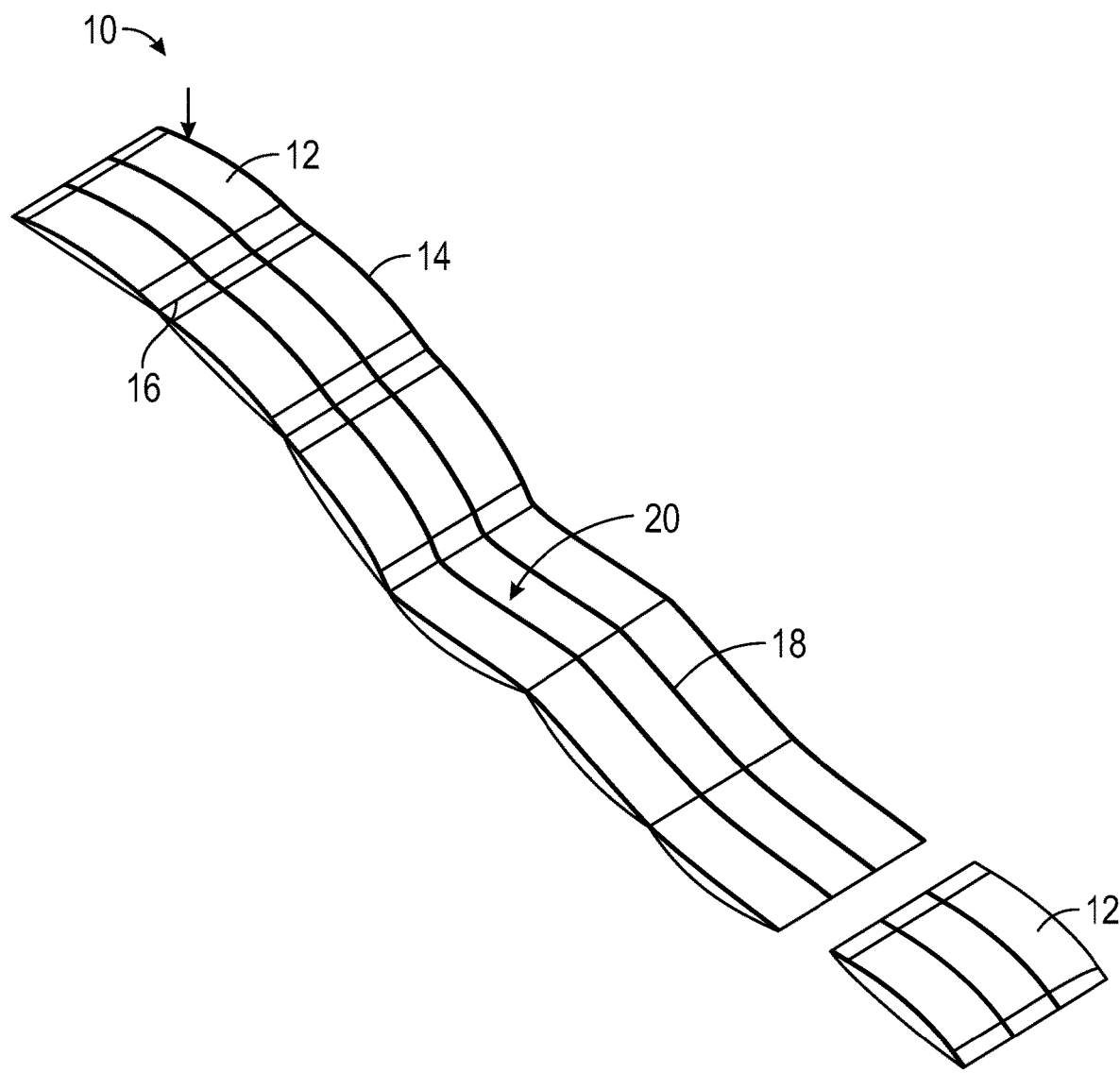
FIG. 2 depicts a perspective view of a small piece of modified strip packaging according to the present disclosure, with a single pouch detached, according to the present disclosure.

In further reference to FIGS. 1 and 2, a continuous circuit is positioned/established over the length of the packaging strip 10, with each of the pouches 12 tagged by a parallel resistor in that circuit. The ends of the respective rails are in electrical contact with leads that complete the circuit. With specific reference to FIG. 2, as each "pack 12" (meaning the pouch as well as the circuitry on it) is removed from the packaging strip 10 by the user, the user also removes a resistor from the circuit and the total resistance of the circuit changes in a predictable manner. Therefore, changes in the resistance of the circuit can be automatically measured/monitored and used to calculate both the number of packs remaining in the strip and the number of packs that have been taken from the strip.

In an alternative embodiment of the present disclosure, the circuitry may be modified relative to the schematically depicted arrangement in which the cross-ties 20 are resistive and the rails 18 are conductive. For example, the material used to form the rails and cross-ties need not have extremely different relative resistances. In fact, the rails 18/cross-ties 20 could potentially be fabricated from the same material with identical conductivity, so long as that material has some measurable electrical resistance. In a further alternative implementation, it is noted that the rails 18 could be resistive relative to the cross-ties 20, as will be apparent to persons skilled in the art. Additionally, the systems and methods of the present disclosure may be implemented with various conductive materials and combinations of conductive materials. Thus, the circuitry may be implemented with any functionally equivalent resistor system layout that provides a measurable change in circuit behavior upon removal of a pouch (and its respective circuitry) from the packaging strip, as will be apparent to persons of skill in the art.

Figure 3:
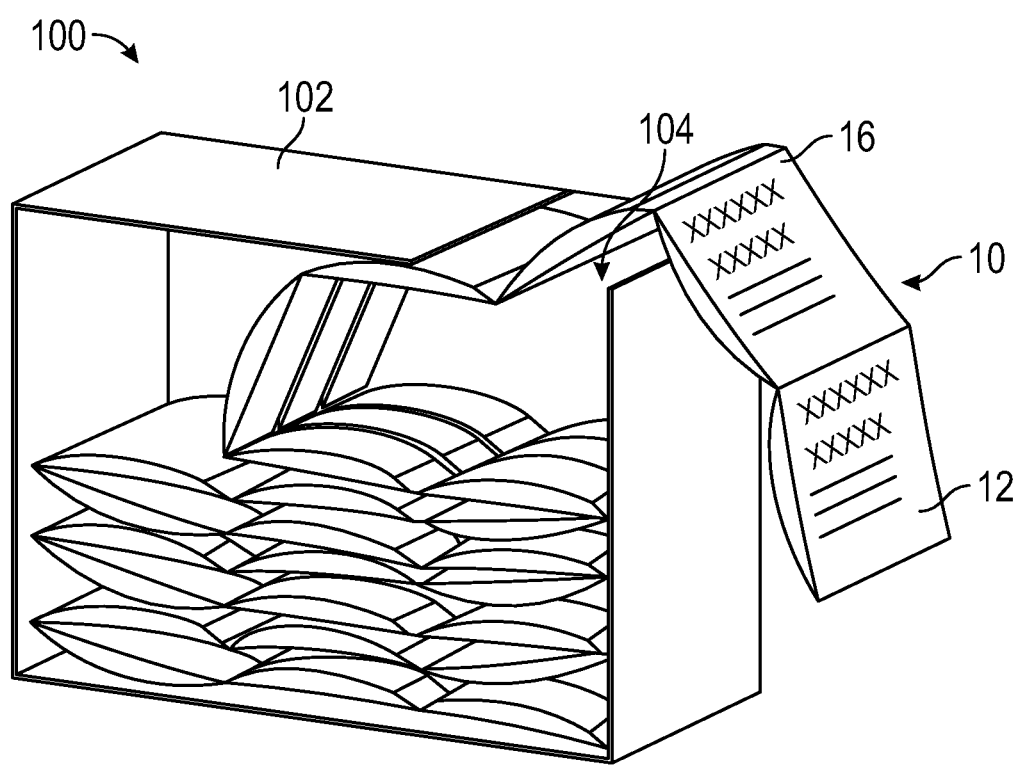
FIG. 3 depicts a perspective view of the small box with the side removed for clarity to show the strip packaging, according to the present disclosure.
Figure 4:
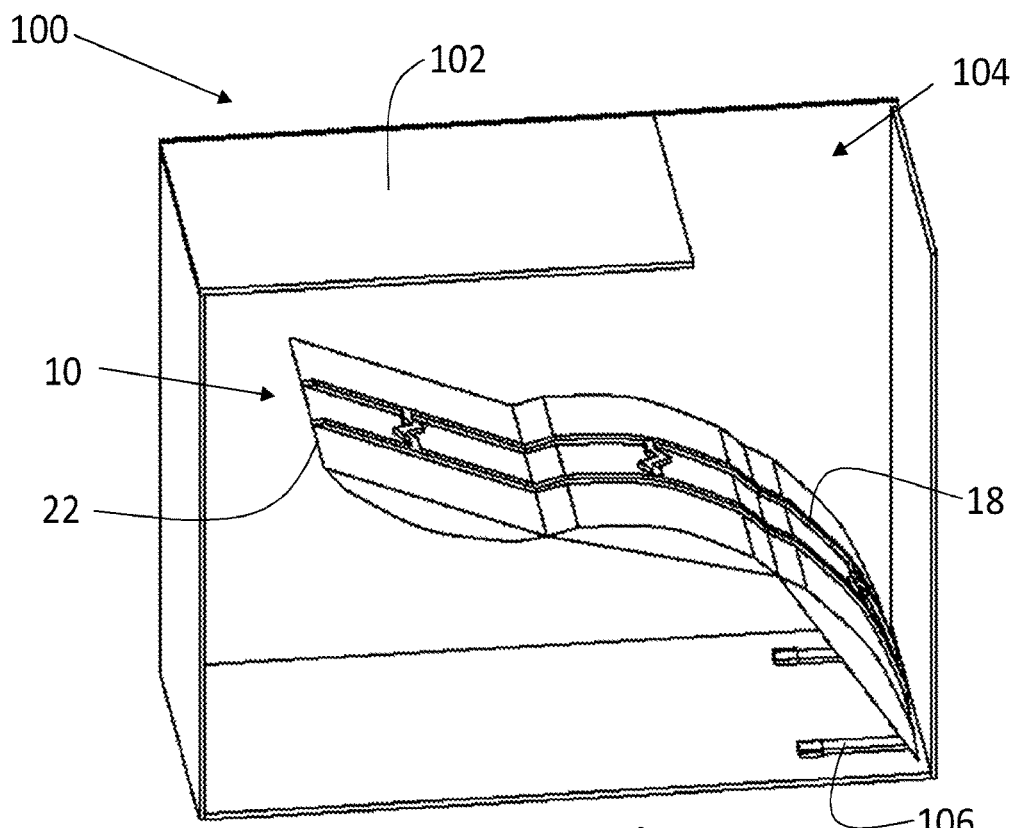
FIG. 4 depicts a perspective view of the small box with the side removed for clarity to show a small piece of strip packaging interfacing with the electrical contacts, according to the present disclosure.
Figure 5:
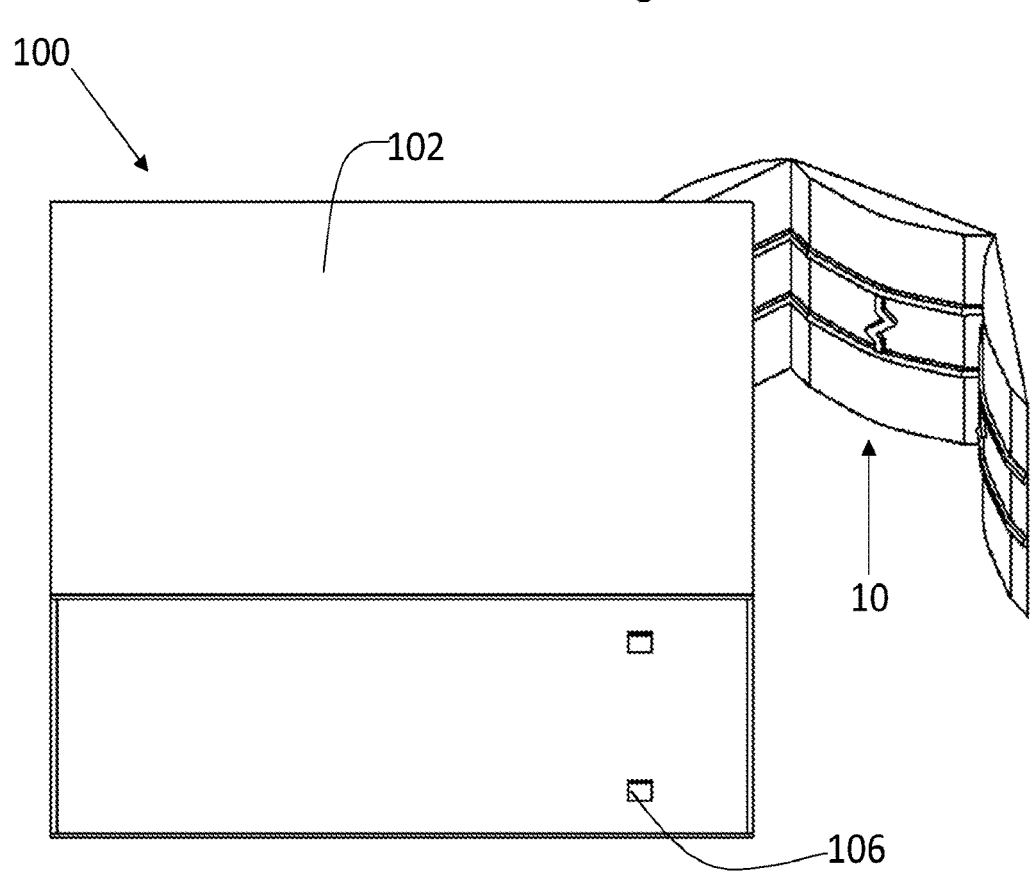
FIG. 5 depicts a bottom perspective view of the small box with a small piece of strip packaging and the exterior surface of the electrical contacts, according to the present disclosure.

Creating Contacts that Allow the Disclosed System to Automatically "Read" the Strips According to exemplary embodiments of the present disclosure, each packaging strip is configured and dimensioned to be loaded into a container/housing (FIGS. 3-5).

For purposes of the present disclosure, the container/housing 102 into which the packaging strips 10 are loaded is referred to as the "small box" 100. In exemplary embodiments, once the packaging strip 10 is positioned within the container/housing 102, the small box 100 is sealed except for an opening 104 large enough for the leading edge of the packaging strip 10 to exit the small box 100.

With specific reference to FIG. 3, with the side wall removed for ease of viewing, the packaging strip 10 is generally loaded into the container/housing 102 in a zig-zag pattern. The sealed lines 16 between the individual pouches 12 generally provide predefined fold axes about which the packaging strip 10 easily folds. With specific reference to FIG. 4, the electrically conductive leads 18 generally extend from the tail end of the strip (i.e., where the last dose in the strip is positioned) to the bottom of the container/housing 102 where they are attached to or otherwise make electrical contact with two electrically conductive contacts 106 positioned on or otherwise accessible within the interior of the container/housing 102. With specific reference to FIG. 5, the contacts 106 are also exposed on the exterior of the container/housing 102. In this manner, the exterior electrical contacts 106 on the container/housing 102 provide a connection site to the electrical circuitry on the strip packaging 10.

Preparing Small Box for Shipping

According to exemplary embodiments of the present disclosure, the front end/leading edge of the packaging strip (i.e., the end where the first dose is located) 22 is positioned so as to be exposed (i.e., stick out) from the opening/slit 104 formed at the top of the small box. The front end/leading edge 22 of the packaging strip 10 is generally folded back onto the top of the small box 100 and detachably adhered relative thereto, e.g., using tape or other securement means. Positioning of the front end/leading edge 22 of the packaging strip 10 in this manner ensures ease of access to the strip for the patient.

To allow the packaging strip 10 to unfold and exit the opening 104 formed in the small box 100 easily (i.e., without tugging or too much friction), the packaging strips 10 cannot be packaged so that they fit too snuggly in the small box 100. Instead, ample room (about the size of a single pack) is generally left between the top of the zig zagging pouches and the top interior of the small box 100 so that the strip 10 has more freedom to move as it unfolds and positions itself to exit the opening/slit 104 formed in the top of the small box 102. This space, however, may pose issues for shipping if left unaddressed, since the packaging strip 10 can move freely in the small box 100. Free movement of the packaging strip within the small box 100 may damage the strip 10 and any modifications to it. To minimize the likelihood of such damage, e.g., during shipping, it is generally desirable to fill some or all of this space with a filler material, e.g., paper (such as tissue paper) or plastic, for shipping. In exemplary implementations, the patient removes the paper or plastic prior to using the system.

Loading of Outer Box/Big Box

With reference to FIGS. 6-10, exemplary implementations of the disclosed system/method are provided, wherein an outer box/big box 210 is provided and is larger than the previously disclosed small box 100. The outer/big box 210 is referred to hereinafter as the "big box". The big box 210 is designed so that the small box 100 can be positioned therewithin, e.g., slid into it from the top. Thus, the top "lid" 214 of the big box 210 is advantageously pivotable so as to permit introduction and removal of small boxes 100. The big box 210 generally includes or defines an angled feed surface adjacent to its front face, i.e., a ramp 216. The ramp 216 is described in greater detail below.

Figure 8:
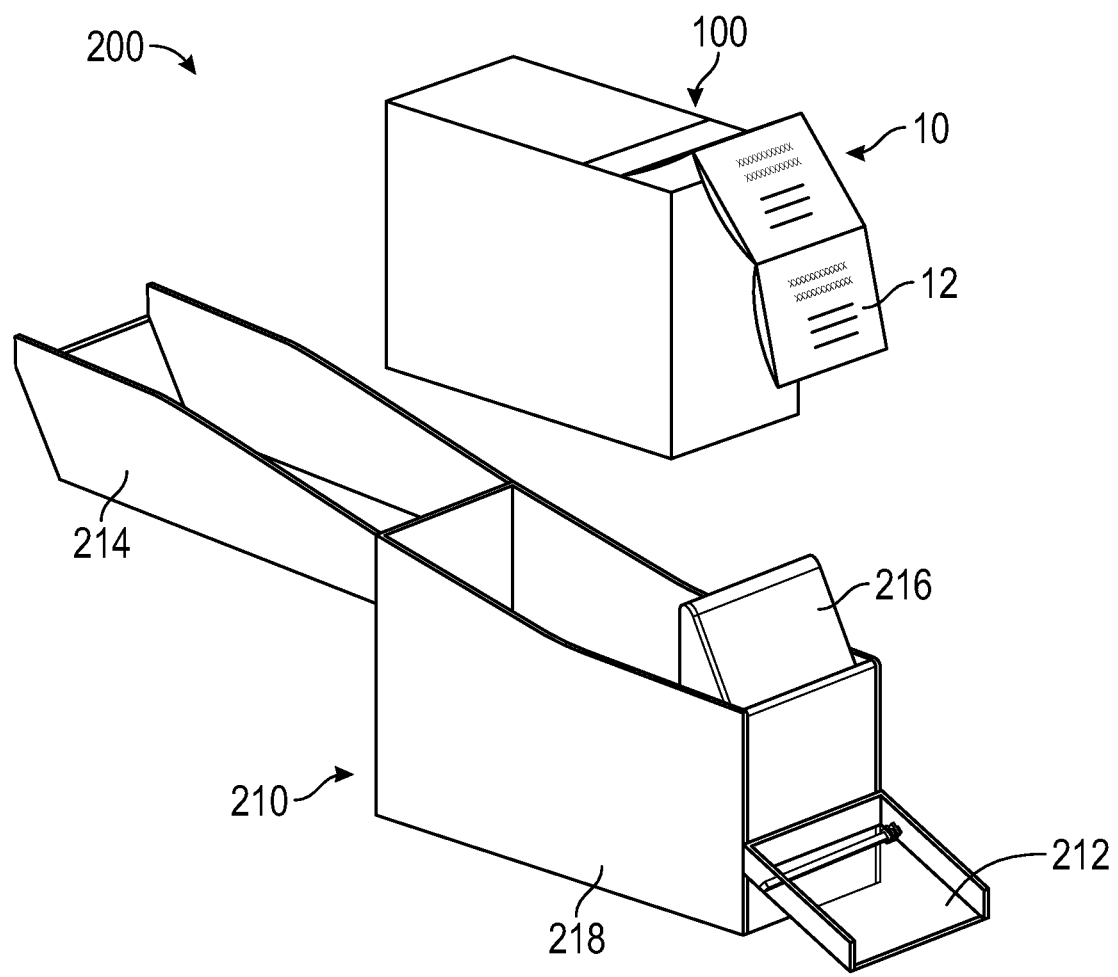
FIG. 8 illustrates the insertion of the small box into the big box (with the lid open) according to the present disclosure.

According to exemplary implementations, with specific reference to FIG. 8, a patient may receive a new small box 100 containing his/her customized strip 10 of individually sealed medication pouches 12 on a periodic basis, e.g., every two weeks or every month. Upon receipt of the new small box 100 and depletion of the inventory of medications in the big box 210, the patient opens the big box 210, removes the empty small box (if there is one), and refills it with the new small box 100 full of medication. It may be necessary to unlatch the child resistant door 212 (described in greater detail below) and/or lid 214 of the big box before the user can open the lid 214 of the big box 210. When open, the separation between the big box 210 and its lid 214 are generally designed to allow the user to use one hand to grab the small box 100 from its sides and pull it out of the big box 210.

Figure 9:
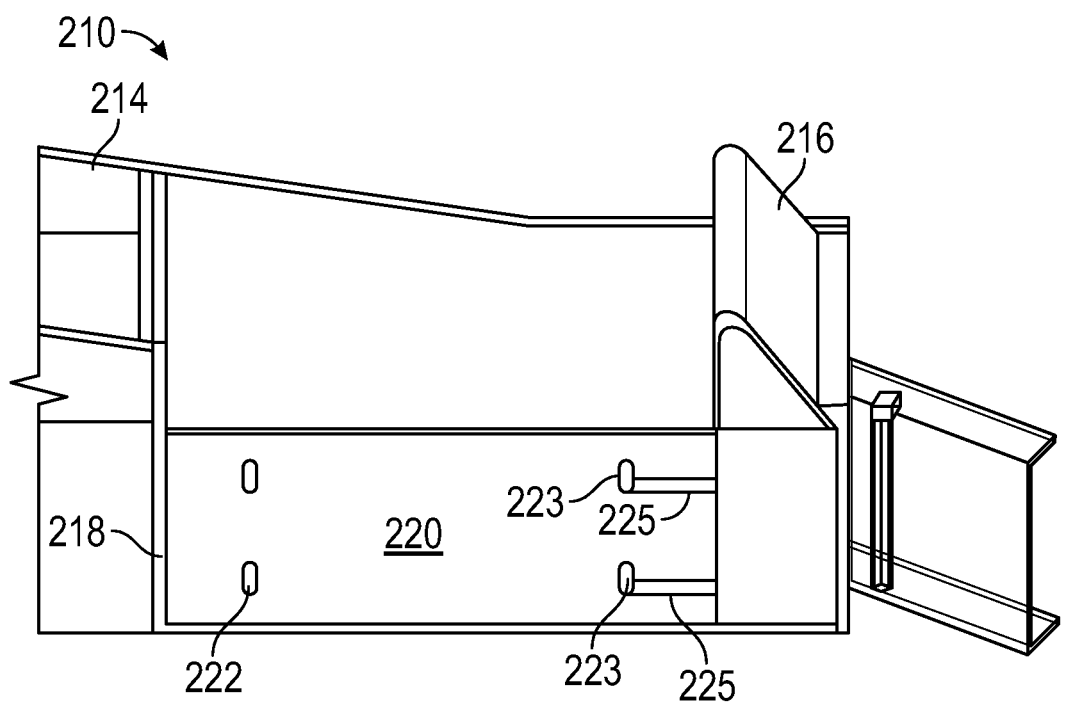
FIG. 9 depicts a top perspective view of an empty big box with the side removed for clarity, and with the safety door open revealing the packaging cutter, according to the present disclosure.

When closing the lid 214, the user may experience some resistance because in exemplary embodiments of the present disclosure, one or more springs 222 are positioned within the big box 210 on the face of the base 220, as shown in FIG. 9. Closure of the lid 214 of the big box 210 will push the small box 100 against these springs 222, providing some ergonomic resistance to closing and providing positional stability to the small box 100 within the big box 210 when the lid is fully closed.

The springs 222 may also function as electrically conductive contacts 223 in the big box 210. Alternative electrical contacts may be employed so long as they are electrically conductive and touching the contacts 106 on the small box 100. Leads 225 run from these springs (or other contacts) 223 to the electrical circuitry that is generally housed beneath the ramp 216. This circuitry will be used to, inter alia, measure the resistance across the packaging strip, determine the number of doses remaining in the strip, determine if the patient is adherent, and provide the appropriate cues to the appropriate parties to assist with adherence. In exemplary embodiments, the ramp and the structure under it are removable so that if a failure in the circuitry occurs, the patient can remove just this one component for repair/replacement. The disclosed circuitry arrangement creates an effective and reliable electrical connection between the circuitry in the big box and the circuit on the strip of medication that ensures accurate and precise measurement. Furthermore, conductive contacts for the circuitry in the big box 210 may instead be placed along the expected travel path of the strip and cooperate with the conductive rails on the strip rather than contacts 106 on the small box. This too may create an effective and reliable connection between the circuitry in the big box and the circuit on the strip of medication.

Complete Circuit

Figure 11:
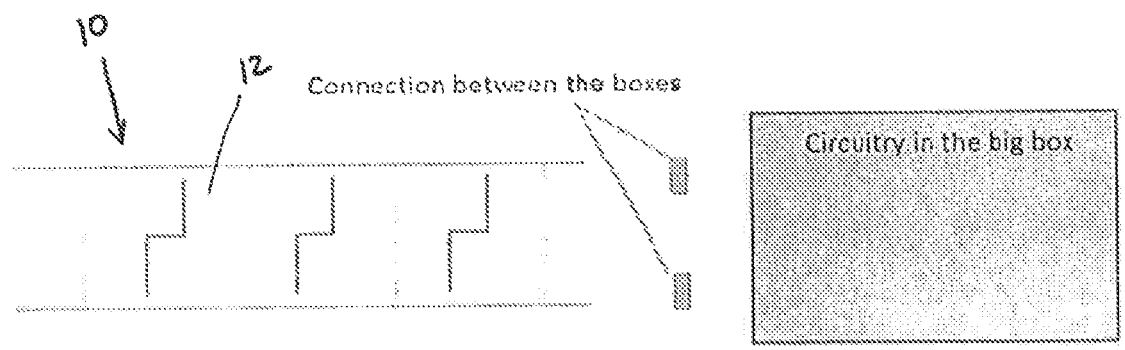
FIG. 11 illustrates the electrical connection between the big box and the strip packaging according to the present disclosure.

According to exemplary embodiments of the present disclosure and in further view of FIG. 11, when the big box 210 establishes an effective electrical connection between the circuitry in the big box 210 and the circuit on the strip of medication, the circuit on the strip of medication is completed and can be read.

The big box 210 is able to use its internal circuitry to compute the overall resistance in the strip 10. If a change in the overall resistance occurs, the circuitry advantageously uses this information to calculate how many packs 12 have been removed from the system by taking advantage of the fact that each of the packs 12 represents a known resistance in parallel to all of the other packs 12. Since the packs 12 are essentially resistors in parallel, the following equation that describes the relationship between parallel resistors in a circuit may be used to calculate the number of packs 12 in the system:

$$\frac{1}{R_T} = \frac{1}{R_1} + \frac{1}{R_2} + \frac{1}{R_3} + \ldots$$

In exemplary embodiments of the present disclosure, each of the packs 12 in the disclosed system has the same resistance across them, and therefore the equation can be simplified to $1/R_{total}$="number of packs"/"resistance across each pack"

Rearranging, the equation yields the "number of packs"="resistance across each pack"/$R_{total}$, where $R_{total}$ is the total resistance on the packaging strip. The "resistance across each pack" will be known (i.e. designed into the system), so to calculate the "number of packs" $R_{Total}$ will need to be measured and calculated by the system.

A known voltage is generally applied to a reference resistor and the circuitry on the strip 10 of medication. The reference resistor and the strip 10 are in series and a chip (e.g., MCU, ASIC, etc.) reads the analog voltage across the reference resistor. The voltages over the reference resistor and the circuit on the strip 10 are directly related to each other since the two are in series (Kirchoff's voltage law). Specifically, the voltage found across either the reference resistor or the strip 10, depends on its resistance relative to the other. The ratio of the voltage of the reference resistor to the voltage of the strip is identical to the ratio of the resistance of the reference resistor to the resistance of the strip. The resistance of the reference resistor is known and the system can measure the voltage across the reference resistor (the system can also assume that the remainder of the applied voltage must be across the strip). With this information the system can calculate the resistance of the strip using the following equations:

$V_{strip}/V_{reference\ resistor} = R_{strip}/R_{reference\ resistor}$ $R_{strip} = R_{total}$(from above)

Figure 12B:
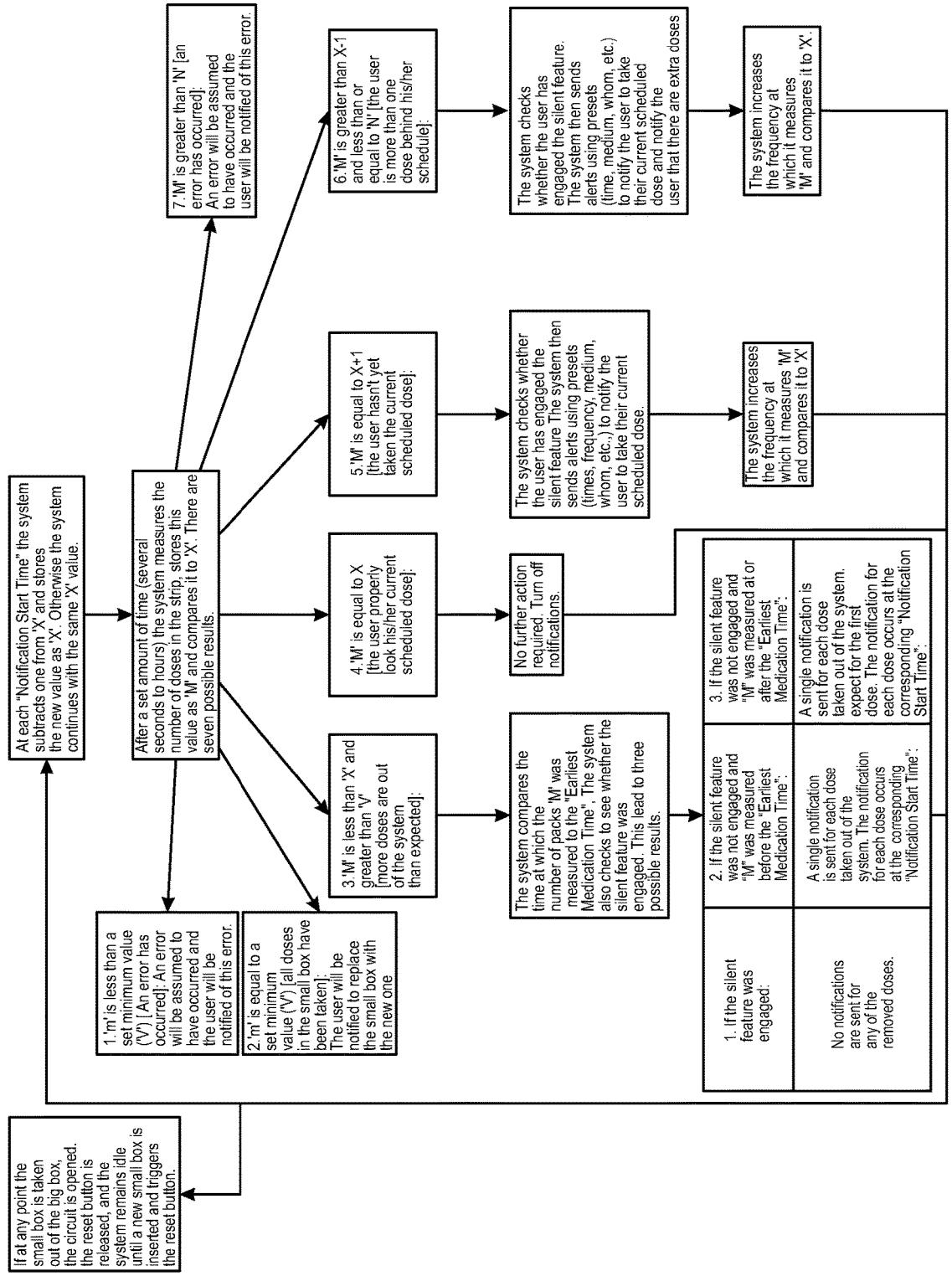

Based on user settings, dose schedules, the calculated number of doses, and other information the exemplary systems/methods of the present disclosure may use a decision tree, such as the one shown in FIGS. 12A and 12B, to determine what function it will perform. The decision tree/flow chart is generally implemented in software/firmware or by way of chip-based circuitry, e.g., an ASIC, as is known by persons skilled in the art. Power can be delivered to the circuitry in various ways, e.g., by one or more batteries mounted with respect to one of the boxes, by a conventional solar power source, and/or by plugging the system into a conventional wall outlet.

Communication-Related Functionalities

According to exemplary embodiments of the present disclosure, conventional communication-related hardware/software may be mounted with respect to the disclosed small box and/or big box. Thus, the disclosed systems and methods may advantageously include and support communication functionalities that allow communication of inventory, status and other information associated with the medications housed within and/or dispensed by the dispensing system to various electronic devices. Similarly, the disclosed dispensing system may be adapted to receive communications from such electronic devices, e.g., commands, settings, inquiries and the like. In exemplary embodiments, the disclosed system includes functionalities that support communication with and to multiple individuals (e.g., the patient, loved ones, family, friends, physician, etc.)

The disclosed communication functionalities are not limited by or to any specific communication hardware/software platform. Thus, various forms of communication may be implemented and supported, e.g., communications based on SIM cards, SMS, MMS, Bluetooth®, RFID, NFC, Wi-Fi®, GPRS, 2g, 3g, 4g, and other forms of radio/electromagnetic wave communication. In addition, the disclosed communication functionalities may be supported/implemented by communicating signals through or on data lines, such as phone lines or Ethernet-based functionalities. Still further, the disclosed communications may be augmented by or replaced with physical cues (such as vibrations), audio/aural cues (such as beeping or buzzing), and/or visual cues (such as a light or moving object).

The disclosed communication functionalities may serve various purposes, e.g., enhancing compliance with medications/prescriptions by providing reminders directly to the patient and/or by providing updates to third parties who can influence compliance by interacting with the patient (e.g., parent, sibling, spouse, friend, health care provider, etc.).

In exemplary implementations of the disclosed communication functionality, the system supports Wi-Fi®-based communications to connect the big box and/or small box to the Internet (directly or through an intermediate communication network) and then, in response to the Internet-based communication, a program is provided that is adapted to send message(s) to the desired recipient(s), e.g., the patient and/or the patient's support network. In exemplary implementations, the noted message(s) may be forwarded to a recipient's phone (e.g., as a text message or other communication modality). It is further contemplated that Bluetooth® and/or a SIM card communication modalities may be employed, e.g., in instances where Wi-Fi® is unavailable or a patient desires a non-phone based communication technique and/or would prefer a wearable electronic device as the receiver for the system-based communications.

The disclosed systems/methods are generally adapted to measure/monitor and communicate various forms of information. For example, the disclosed system/method may be adapted to measure/monitor essentially any information relating to the number of packs in the system and the time of day. Further exemplary data that may be measured/monitored and communicated include (i) low battery condition, (ii) if a large number of packs are taken out of the system (e.g. tell loved one and patient) based on a preset/customized threshold, (iii) reminder notification(s) at set time(s) to take a dose (e.g., tell patient), (iv) notification(s) at a set time only if the patient hasn't taken his/her dose (e.g., tell patient and physician), (v) notification(s) if it is too late to take a dose and the dose should be skipped, (vi) notification(s) if the incorrect dose is taken at the incorrect time, (vii) notification(s) to reorder medication (e.g., tell pharmacist, patient, and loved one), and (viii) notification(s) if the child resistant lock is not engaged. Additional notifications and/or communications may be implemented according to the present disclosure without departing from the spirit or scope of the present disclosure, as will be readily apparent to persons skilled in the art.

The settings for the device (e.g., reminder times, notification intensity/frequency, who gets notified what and how, etc.) are generally subject to modification, and may be customized by the patient and/or the patient's support network. Modifications may be implemented by the patient using online communications, e.g., using a web portal or a smart phone, or in a non-direct manner, e.g., using a phone or other communication modality/electronic device to facilitate the modification (e.g., calling a pharmacist to arrange for an online change to the settings). The individual device/system would then grab/receive these updated settings from the Internet over Wi-Fi® (if the patient does not have or is not using the Internet for the noted purpose, the device/system could grab/receive the updated settings using data packets it receives through a SIM card). The patient could also connect directly to the device over Wi-Fi®, and use a web portal to directly change the settings on the device. The patient could also use Bluetooth® or NFC to change the settings (e.g. using the patient's phone). In exemplary embodiments, the settings may be uploaded via USB, touch screen or a physical interface (e.g., buttons). In essence, any conventional forms of communication modality could be used to change the settings, as known to persons skilled in the art.

Additional Features/Functions
Child Resistant Functionality

Figure 6:
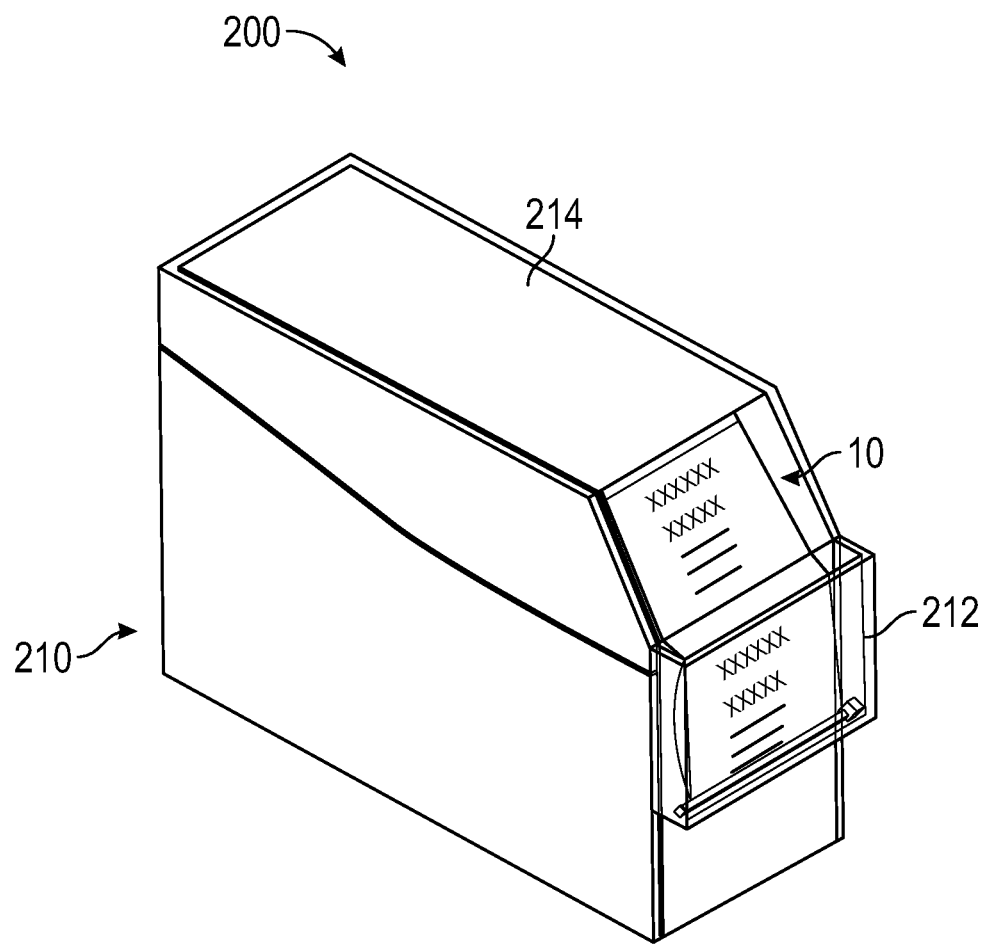
FIG. 6 depicts a perspective view of a big box encased around the small box according to the present disclosure.
Figure 7:
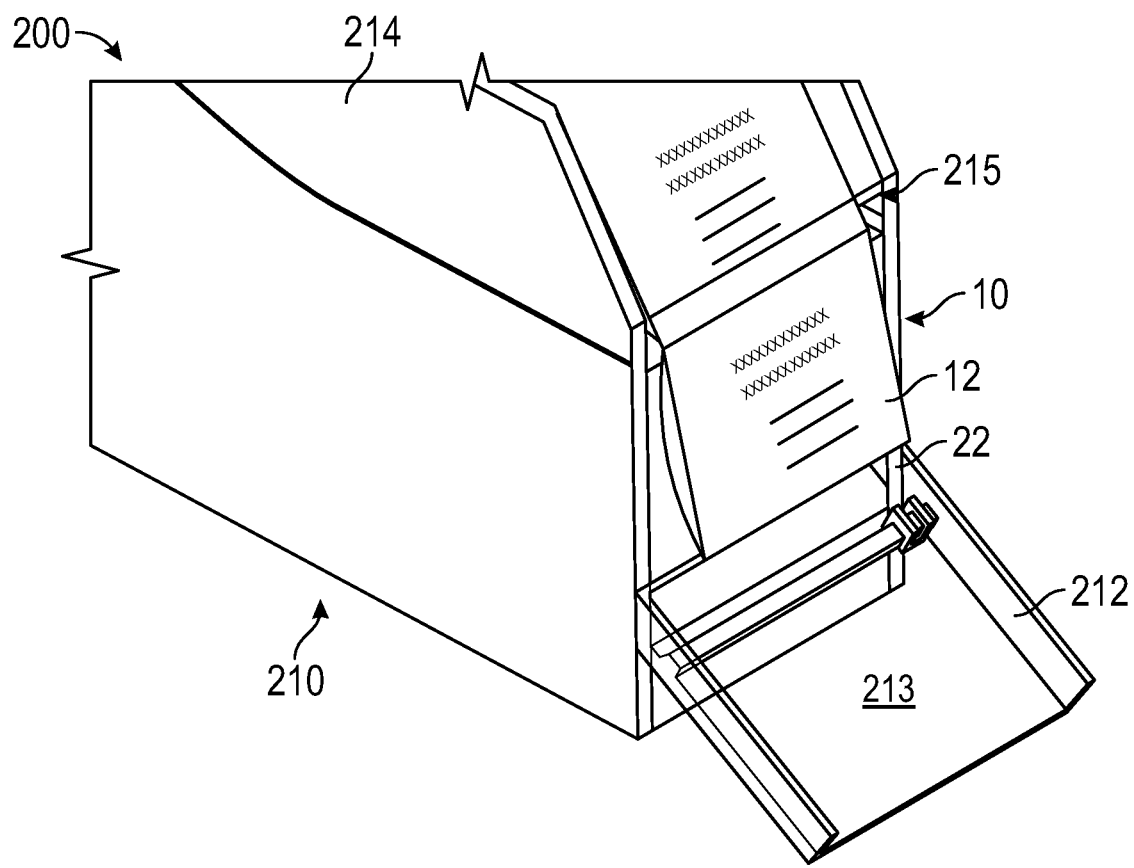
FIG. 7 depicts a close-up perspective view of the front of the big box, encased around the small box, with the shielding door open, according to the present disclosure.

According to exemplary embodiments of the present disclosure, the dispensing system includes child resistant functionality to prevent access to the medication in a child resistant manner, i.e., pass applicable PPA guidelines. For example, a child resistant door may be used to prevent or allow access to the medication at the user's discretion. As shown in FIGS. 6 and 7, the strip 10 is sticking out of an opening/slit 215 formed in the front face of big box 210 and the patient can close the door 212 over both the portion of the strip stick out of the slit/opening 215 and over the slit/opening itself. This door may then lock and unlock in a manner that is child resistant, thereby protecting the medication in the big box 210 by a means that satisfies PPA guidelines.

With reference to FIG. 7, the leading edge 22 of the packaging strip 10 is accessible to the user/patient from the exterior of the outer box 210. The outer box 210 is designed to allow a preset number of packs/pouches 12 to hang out of the outer box 210 without the strip being deformed or the medication at risk of being damaged from the opening or closing or locking or unlocking of the child resistant door 212. For this embodiment that number is one. With reference to FIGS. 6 and 7, the door 212 is advantageously moveable relative to the outer box 210 to either allow or prevent access to the medication therebehind. In this embodiment the door is vertically pivotable. In reference to FIG. 6, when the door is pivoted up it prevents access to the leading edge 22 of the strip of medication and is said to be in the closed position. In reference to FIG. 7, when the door is pivoted down it allows access to the leading edge 22 of the strip of medication and is said to be in the open position. The door may lock in the closed position in a manner that is child resistant. The door 212 is advantageously fabricated from a hard plastic material that is see-through, thereby permitting a user/patient to see his/her next dose/pouch 12 through the door 212.

In use, after accessing and separating the next dose of medications 12 from the packaging strip 10, the patient (e.g. an elderly patient with arthritis and no children in the household) can choose to leave the door 212 open and, if desired, disengage/remove the door. Of note, the lid 214 may have its own separate child resistant lock or be locked in a child resistant state by the door when the door is in its closed position.

In an alternative embodiment, the disclosed door 212 may slide on a track rather than pivot relative to a hinge. In the "slide door" implementation, the user/patient would be able to open the door 212 by sliding the door on tracks that are defined/positioned on the face of the outer box 210. In alternative embodiments, the child resistant covering could be flexible instead of a hard material. For example, a polymer mesh, fabric, or other compressible, expandable, or elastic material(s) could be used. The material or combination of materials and their construction are selected so as to control access to the doses (through actions by the user). For example, a plastic mesh could be pulled over the doses/packs 12 sticking out of the slit 215 in the big box 210 and lock into place, to prevent access to the doses/packs 12. The same mesh could then be unlocked to uncover the doses/packs 12 and allow access to them.

Ramp

Figure 10:
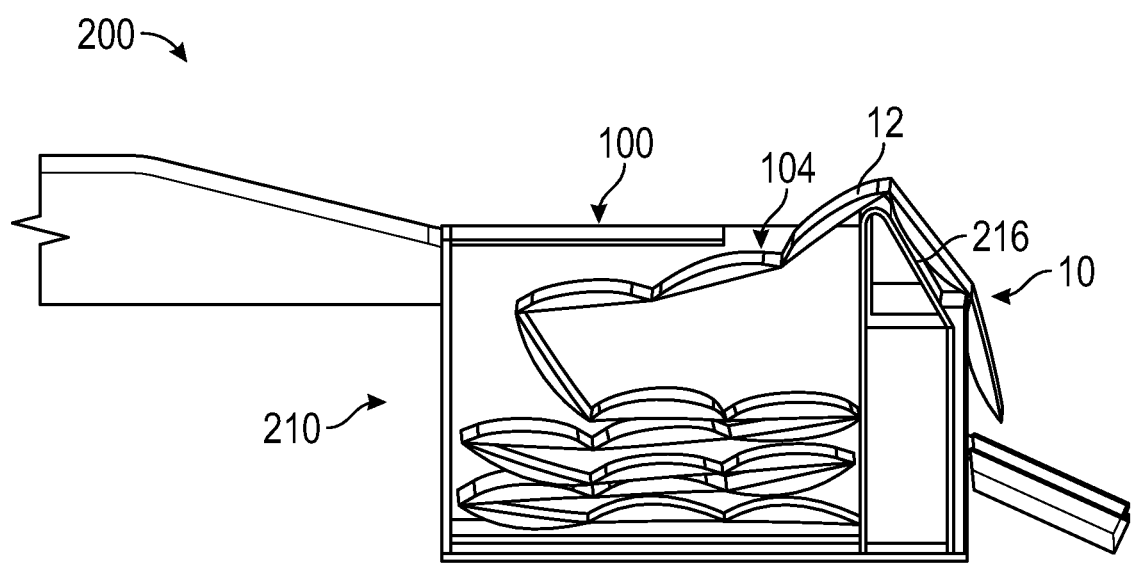
FIG. 10 depicts a side view of a fully packaged big box with the side removed for clarity revealing the side box and the strip packaging, according to the present disclosure.

With reference to FIG. 10, the ramp 216 acts to provide a stable path in order to direct the strip 10 from the opening 104 in the small box 100 to the slit 215 in the big box 210. It helps to make it comfortable for the user to remove the strip from the big box 210. There are numerous alternatives to using a ramp to direct the strip (e.g., axles (stationary and rotating), pulleys, wheels (stationary and rotating)). The space beneath the ramp may be used to house the circuitry in the big box 210.

When the strip is exiting the small box 100, it is ascending relative to a horizontal axis. The weight of the packs 12 are pulling the strip 10 back into the small box 100. However, since the strip 10 bends over the apex of the ramp 216, the weight of the packs descending to the slit 215 in the big box 210 and the friction they experience with the ramp 216 advantageously prevent the strip 10 from being pulled back into the small box 100.

Another feature of the ramp 216 is that its highest point is generally higher than the opening 104 in the small box 100. This relative positioning of the disclosed structures helps to ensure that when the strip 10 is under tension and being pulled over the ramp 216 and out of the big box 210, that it does not have to contact the sharp edges of the opening 104. This travel path reduces the risk of damage to the strip 10 and any modifications (such as electrical tags) to it by being tugged against the sharp edges at the opening 104 in the small box 100.

The ramp 216 also advantageously encourages the packs 12 to be pulled out in discrete steps. As the strip 10 travels over the top curve/apex of the ramp 216 where the medication is redirected, the pills/tablets are generally squeezed to the bottom of the pack. To get the lump of pills in the pack over the curve/apex of the ramp 216 requires some additional force (the ramp 216 is generally curved at the top so that friction between the ramp and this lump is not significantly large, so that too much force is not required and to prevent possible damage to the strip). Ultimately, this extra force to pull the pack over the ramp 216 and the immediate drop in required force after the lump passes the apex, gives a discrete tugging sensation every time a new pack 12 is pulled over the apex of the ramp 216 and out of the slit 215 in the big box 210. This provides physical feedback to the patient so that they know they have pulled out a single dose. The angle of the ramp 216 also allows creation of an optimal viewing angle for the next dose to exit the slit 215 in the big box 210 as seen through a window 213.

Window

According to exemplary embodiments of the disclosed system, a window 213 is provided in the lid of the big box 210. The big box is designed so that patients can have packs hanging outside of the big box and see the next pack inside the big box through the window.

Silent Feature

When a patient removes packs from the strip hours (the specific time may be set by the user and/or another party) before their scheduled dose time, according to exemplary embodiments, the user will then have two choices at that point, either (1) allow the system to send a reminder for each of those packs at designated reminder times or (2) "silence" the system so that it will not send reminders for any of those packs. By default, the system is generally programmed to choose option 1 every time packs are removed hours before their scheduled dose time. However, the ability to over-ride this default setting, i.e., switch to option 2, is useful in many instances, e.g., when a person takes his/her morning and evening packs with him/her every morning to work and on some days doesn't want a reminder for the evening pack. Of note, the ability to switch to option 2, i.e., over-ride the default setting, could be effectuated by the user in various ways, e.g., the user could activate the "silent" feature by replying "silent" to a text or email, for example A button or other control feature could be positioned/actuated on the big box and/or small box to toggle between option 1 and option 2. Furthermore, a similar silent feature could also be enabled for missed doses so as to halt any reminders for the missed dose. In any case, exemplary embodiments of the present disclosure allow the user and/or other individual to establish a silent mode such that one or more reminders are not forwarded to the user and/or the user's network, as described herein.

Portable Version

According to the present disclosure, a portable version of the system may be provided, e.g., for a person who travels or is otherwise called away from his/her home base. The portable version may be advantageously adapted to cooperate with the "shortened" strip of multiple packs taken out of the home base system, e.g., by clamping the portable version of the system onto the tail end (the last dose) of the shortened strip. In exemplary embodiments, the clamp would pierce through a small portion of the last pack (without damaging the medication) to create conductive contact with the electrical circuitry on the strip. It could then perform most of the same functions as the home base system as described above. The shortened strip could wrap around this portable version for storage and deployment purposes.

Side Box

Figure 13:
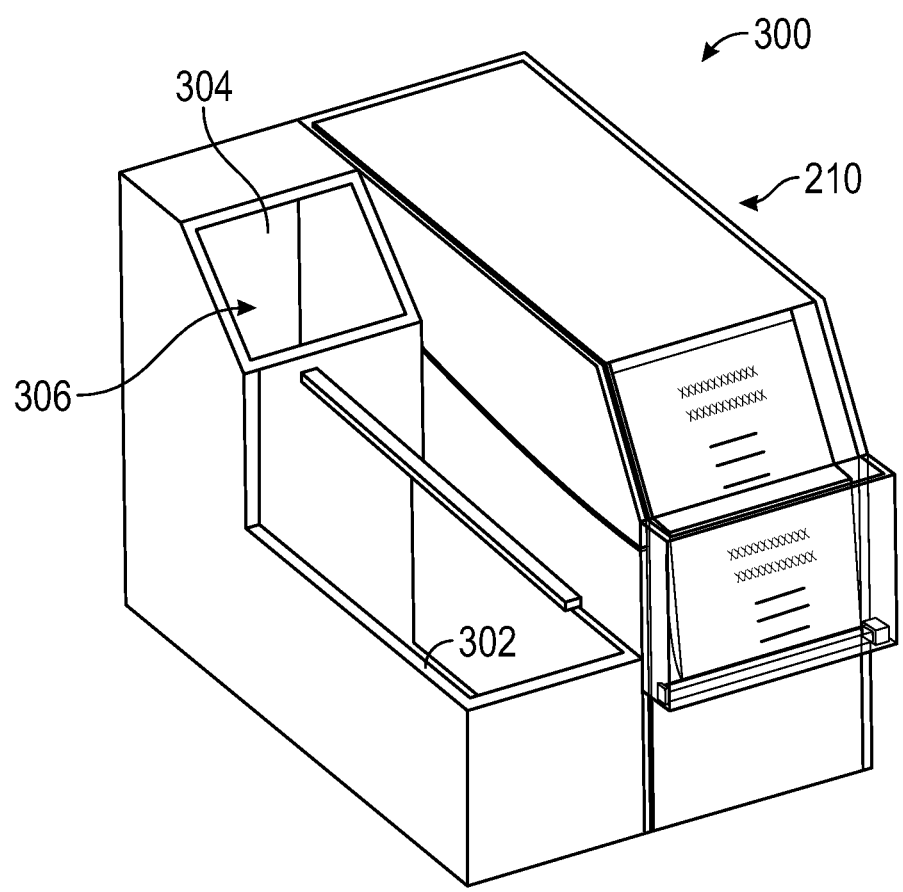
FIG. 13 depicts a perspective view of the big box with a side box and a trash can attached to the side, according to the present disclosure.

According to exemplary embodiments of the present disclosure, a smaller box may be deployed on the side of the big box. With reference to FIG. 13, the smaller box 302 may advantageously include a lid on a hinge. This smaller box 302 would function to allow the patient to store other medications that may not fit in the packs (e.g., ointments or inhalers) or new medication that was prescribed to the patient after his/her order for the strip was made. The smaller box 302 may function as a "smart box," that knows when it has been opened. For example, it may have a button on it that is constantly pressed while the lid is closed and when the lid opens, the button would not be pressed down. The system would be able to tell when and if the lid was opened during the day and the user might then be able to set reminder times for the side box 302, e.g., to promote/ensure adherence in use of the smaller box's contents. In exemplary embodiments, the smaller side box 302 would include or tap into communication functionalities of the type described herein with respect to big box 210.

Trash Can

With further reference to FIG. 13, in exemplary embodiments, behind the smaller side box 302 and to the side of the big box 210, a trash can/receptacle 304 may be provided with an opening 306 that is at an angle. The angled opening 306 allows trash to be placed in the receptacle 304 from above and from the front (while giving a backboard to push the trash against). The trash can may also be removable from the system.

Pack Separation Assistance

According to exemplary embodiments of the present disclosure, the patient is easily able to separate doses along the perforations with his/her bare hands. For others who may find this difficult a device to cut/damage/perforate/tear a pouch on the strip (e.g. at the separation 16 between each sealed pouch of medication), clamp/hold the strip in a specific position, or another device to help separate the packs from their strip may be provided. Positioning of a child resistant slide cutter on the bottom of the child resistant door 212 may be advantageous so that when the door 212 is opened, the bottom of the child resistant door 212 will turn on its hinge and turn the slide cutter with it so that the slide cutter is exposed at an advantageous position and angle for use. Furthermore, at the slit/opening 215 in the big box 210 a material that resists the movement of the packaging strip against its surface can be strategically positioned (e.g. at the bottom lip of the window) so that the user may easily pull the packaging strip out of the slit/opening 215 at a particular range of angles and then by readjusting the angle at which they pull the strip out of the slit/opening 215 (e.g. at an angle that forces contact with the strategically positioned material), the material can hinder the strip from being pulled out of the big box 210 any further. With the movement of the strip hindered, the user could then easily remove their desired pouches from the rest of the strip, possibly with a single hand. Alternatively the system may be designed so that the user may clamp down at a specific location on the strip with a portion of the big box 210 or lid 214 by applying pressure to some location on the container. This clamping force would hold on to the strip so that the user could remove their desired doses with their remaining free hand. To prevent the clamping mechanism from destroying medication, the clamping material may be constructed from a compressible/deformable material. In addition to the exemplary embodiments described herein, various alternative implementations are specifically contemplated.

Capacitance and Inductance

Instead of resistors, it is noted that capacitors, inductors, or other electrical components can be used as the cross-ties, and act as the tags/indicia on the strip. Removal of a pack from the strip would then cause a measurable change in the component's respective electrical property (e.g., capacitance or inductance). If the change in the electrical property is predictable and measurable (as known to those skilled in the arts) it can be used to calculate when and how many doses are removed from the system.

The strip can be turned into a large capacitor. A conductive material (e.g., conductive tape, conductive mylar, etc.) can be placed on both faces of the strip on the sealed side of the strip (so that the distance between the two coated faces remains constant). The conductive material on either face would never contact. A voltage drop would then be created across the conducting materials on the strip, creating a capacitor. When a pack is removed from the strip, the capacitance of the strip would change, and this change could be measured to calculate the number of packs in the strip.

Figure 14:
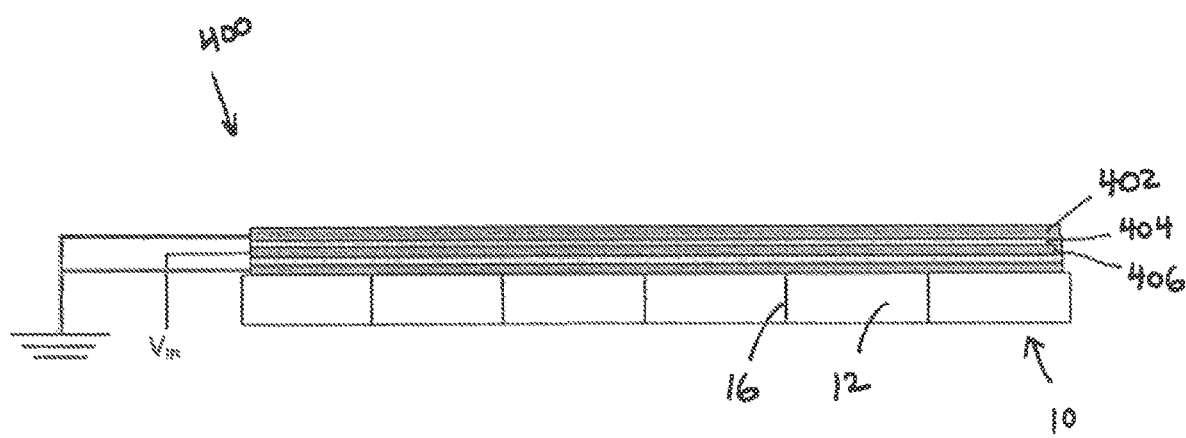
FIG. 14 depicts a side view of a flexible strip capacitor, attached to the strip packaging, that can be used to track the number of packs, according to the present disclosure.

With reference to FIG. 14, an alternative modification that can be made to the strip for tracking the number of doses in the strip utilizes a flexible shielded capacitor (a "strip capacitor") 400 that may be adhered along the length of the strip 10 on one face/side. When a unit 12 is removed from the strip of medications 10, a portion of the strip capacitor 400 is removed as well. Since capacitance is directly related to the surface area of a capacitor, the number of units remaining on the strip can be calculated from a measurement of the capacitance of the strip capacitor 400.

The strip capacitor 400 is generally made by layering thin conductive materials and flexible dielectric materials. In general, the strip capacitor 400 consists of two grounded exterior conductive layers 402, at least two dielectric layers 404, and at least one interior conductive layer 406. Additional conductive and dielectric layers could be added inside of the grounded exterior layers. The strip capacitor 400 can be produced on its own and then adhered to the exterior of the strip packaging 10 on one side/face, and laminated with another plastic layer if needed.

Using similar methods as those described above, the strip capacitor 400 may be connected to electrical circuitry in the big box (not shown). The interior conductive layer 406 receives a voltage input ($V_{in}$) that charges and discharges the capacitor, and the capacitance between the internal layer and the external layers can be calculated by various means. For example, an alternating voltage input could be applied to the capacitor according to the rate at which the capacitor charges and discharges (i.e., using an analog oscillator such as a 555 timer or a digital oscillator). In this case, the capacitance would be inversely proportional to the frequency of the oscillating signal and could be easily measured with a digital pulse counter using a proportionality constant determined by the circuitry involved.

In a rectangular parallel plate capacitor, capacitance is given by Capacitance=$\varepsilon$kLW/d, where $\varepsilon$ is the permittivity of free space, k is the dielectric constant of the dielectric layer, L and W are the length and width of the capacitor area, and d is the separation distance between the plates. In a long rectangular strip with removable sections, all parameters are constant except L, so a measurement of capacitance is directly proportional to the length remaining on the strip at a given point in time after some amount of length has been torn off by the user. This information can be used to determine the number of packs remaining on the strip.

Since the strip of medications 10 is bent or wound sharply back across itself in the device, the materials used for the conductive and dielectric layers must be very flexible. Plastics such as polyesters and vinyl are two possible fabrication materials, though other materials may be selected subject to the noted performance criteria. The distance between the layers should be manufactured to be consistent across the whole strip and constant under bending of the strip. Another consequence of the folded strip is that a standard two layer capacitor would experience significant inductive effects as the portions of the strip are positioned near to each other. Thus, the grounded exterior layers 402 are essential to shield the capacitor and maintain a stable capacitance.

Figure 15:
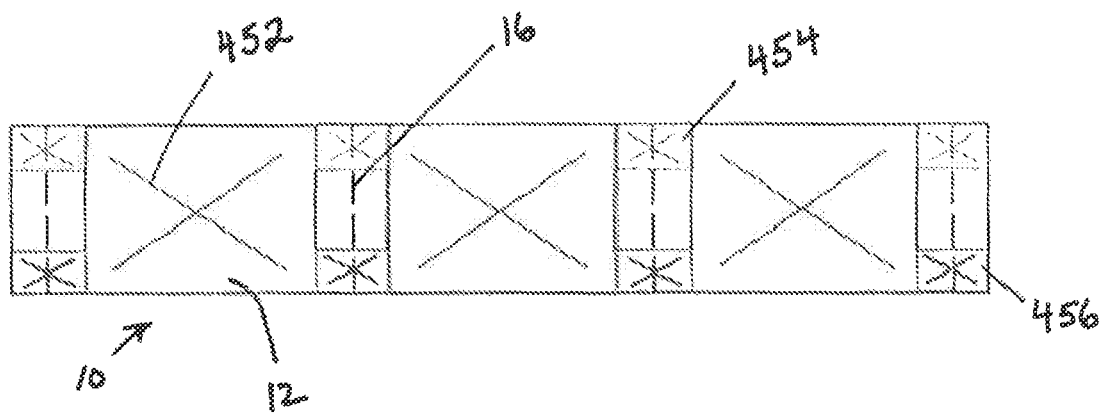
FIG. 15 depicts a top view of the strip capacitor attached to the strip packaging according to the present disclosure.

Another technical challenge associated with this system is that when a section of the strip is torn off, the interior 406 and exterior conductive layers 402 are at risk of shorting at the exposed end of the strip. To avoid this undesirable development, with specific reference to FIG. 15, the long rectangular layers of conductive material that make up the interior 406 and exterior 402 conductive layers can be replaced by discrete rectangular units 452 (indicated by the larger x's) that match up with the packs of medication 12 and are separated by a small distance at the places where the packs are separated and are to be torn 16. The small rectangular surfaces 452 are connected by thin sections of conductive material. These sections are positioned on one side of the strip for the exterior conductive layers (the "top" x's) 456 and on the other side of the strip for the interior conductive layer (the "lower" x's) 454 such that there is no opportunity for the interior and exterior layers to contact each other at the section where the packs are separated and will be torn 16.

Multiple Circuits

Each pack in the strip could make a unique circuit in the system so that the removal of a pack 12 from the strip 10 would break an entire circuit (i.e., current can no longer flow through that particular circuit). In this way, the disclosed system would be able to tell which dose has been removed and when.

A system/design whereby movement of the strip through the container causes a circuit in the system to close or open depending on the location/movement of the strip 10 in the container. This can be achieved through strategic placement of switches/conductive sensors and strategic modification of the strip with conductive and resistive material and/or adding or removing material from the strip. This information on the closing and opening of the circuit can be used to index how many packs 12 have been removed from the system. This assumes that the displacement of the strip is directly and predictably related to how many packs have been taken from the system.

Determining Displacement and/or Status and/or Position of the Strip without Indicia/Tags While the strip is traveling over an axle/pulley/roller, forcing it to rotate as the strip travels over the axle/pulley/roller, the number of rotations of the axle/pulley/roller could be measured and used to calculate how much of the strip has traveled over it and, therefore, how many doses have been taken from the system. This assumes that the displacement of the strip is directly and predictably related to how many packs have been taken from the system.

The strip could be rolled around an axle/roller/pulley and as it unwinds from its roll, the number of rotations of the axle/roller/pulley could be measured and used to calculate the number of packs taken from the strip. This assumes that the displacement of the strip is directly and predictably related to how many packs have been taken from the system.

In exemplary embodiments, the medications in each pack 12 create a bulge in each pack 12. While the strip 10 is traveling up the ramp 216 through the small box 100, a guiding structure (e.g., squeegee-like structure) could be positioned in the travel path so as to push all of the medicine to one side of the pack 12 as the strip passed the guiding structure. This translation of the medications to a specific region creates a bulge of medication at only one part of the pack 12. At the top of the ramp 216, a lever (not shown) may be positioned so that it is flush with the strip 10 and ramp 216 and extends the width of the strip 10. When the empty portion of the strip 10 is passing between the lever (not shown) and the ramp 216, the lever (not shown) is "inactive" (i.e., it is very close to touching the ramp, but with the strip in between). However, when the bulge of medication passes through this point, it "activates" the lever (not shown), by pushing it up and increasing the distance between the ramp 216 and the lever (not shown). This activation can be measured in several ways (the displacement of a spring attached to the lever, a button that the lever presses when it is "active", a sensor that detects if the lever is in a particular position, a flex sensor that changes shape when the lever activates, etc.). In this way, pack-by-pack advance may be indexed through activation of the noted lever (not shown).

This assumes that the displacement of the strip is directly and predictably related to how many packs have been taken from the system.

A scale could be used to measure the mass of the packs 12 in the system. A change in mass would mean packs have been displaced from the system and this could be used to calculate the number of packs 12 in the strip 10.

Furthermore, electromagnetic waves (e.g., IR, light, etc.) and/or mechanical waves (e.g., sound, ultrasound, etc.) may be used to determine the location/status of packs along their expected travel path without the use of indicia or modifications to the strip. For example, a camera image (produced by electromagnetic waves) could be analyzed for the presence or absence of the strip/packs by looking for the particular color of the strip/packs against a contrasting background or by looking for sharp borders of the strip within the image. In another embodiment, electromagnetic or mechanical waves could be directed at specific points along the expected travel path of the strip and their reflection and/or transmittance may be measured to assist in determining the location of packs and/or the number of packs that have passed by a specific reference point. This information could be used to approximate the total number of packs/doses remaining in the strip. This information may also be used by the system to approximate whether the system has been loaded correctly, if a person is interacting/engaging with the system, and if the location of the strip/packs is not within the bounds measurable by the system (i.e. if the strip physically extends to/beyond the physical bounds where the system is expected to reliably approximate the number of packs in the strip).

Example of an Indicia-Reading System Combined with System that does not Use Indicia/Tags An example combining some above-mentioned methods involves the use of barcodes, barcode scanner(s), proximity/distance sensor(s), and motion sensor(s). The strip will be housed in a container/enclosure where it will follow an expected travel path out of the container/enclosure for it to be dispensed/accessible to the user. The strip will be placed into the container such that the last dose (the tail end of the strip) is to be dispensed last from the container and the doses are to be dispensed/accessible in sequential order. The following sections will discuss the individual components of this system and how they can be used in systems to determine or assist in determining the number of packs remaining in the strip.

Barcodes and Barcode Scanner

In one embodiment, the barcodes could be placed (by directly printing on the strip, attaching adhesive labels, gluing labels, etc.) on the back face (the face not directly visible to the user, during typical use) of the strip. In another embodiment, the barcodes could be placed on the front face (the face directly visible to the user, during typical use) of the strip. In either embodiment, the barcode scanner(s) would be positioned at some physical location in the system so that the scanner(s) can scan the barcode(s) on the strip at some particular point(s)/region(s) in space along the expected travel path of the strip. Of note, the barcodes mentioned in this embodiment can be replaced by another tag/indicia mentioned or alluded to in this document and the barcode scanner replaced by the electrical device most appropriate to cooperate with that respective tag/indicia (as known to those skilled in the arts).

The barcodes could be oriented perpendicularly or parallel/antiparallel to the length of the strip or any orientation in between. A scanner must be oriented/positioned so that it may scan the barcode(s) on the strip; however, the position of the scanner(s) in the system may vary through the strategic use of mirrors or other devices that can manipulate the travel path of the medium that allows the tags/indicia and electrical device(s) to cooperate. The size, type, and number of scanners may vary between embodiments.

The scanner(s) could be set to scan at specific times, by user input (e.g. user pushes a button, etc.), when the system determines that the user is interacting/engaging with the system (begin scanning as soon as the user begins to use the system or wait until the user is finished using the system), or the scanner could be kept on at all times. The system would then use the information from the scanned barcode(s) to determine the number of doses/packs in the strip.

Below are a few examples of scanner setups that could be used for barcodes that are oriented perpendicularly to the length of the strip (these examples can be adapted and modified for barcodes at another orientation):

There could be a single linear scanner (CMOS, CCD, laser, linear imager, etc.) oriented perpendicularly to the length of the strip (and parallel/antiparallel to the barcodes) and positioned at a point in the system so that it may scan for a barcode on the strip at a specific point along the strip's expected travel path. If the scanner is on at all times or turns on when the system approximates that it is being used (e.g. it detects movement likely caused by the user), the scanner could scan barcodes as the user pulls the strip out of the system and the barcodes move through the scanning region. The barcodes on the strip can be large in size and/or in frequency to improve the odds that a barcode will be scanned in the scanning region. The system would use the information from the scanned barcode(s) to approximate the number of doses/packs in the strip.

There could be multiple linear scanners, positioned so that they each may scan for barcodes at a different point along the strip's expected travel path. This would improve the chances of scanning at least one barcode in a region of space along the strip's expected travel path while the strip is stationary or moving. Furthermore, the scanners could be strategically positioned and barcodes arranged (in size, density, and location) so that while the strip spans the scanning region, there will be at least one barcode in the scanning region of at least one scanner.

Raster scanner(s) (as known to those skilled in the arts) may be used in order to scan multiple points along the strip's travel path with a single scanner. This would improve the chances of scanning at least one barcode in a region of space along the strip's expected travel path, while the strip spans that scanning region. Furthermore, the scanner(s) could be positioned and barcodes arranged (in size, density, and location) so that while the strip spans the scanning region, there will be at least one barcode that can be scanned. The barcodes would also need to be positioned and sized so that they can completely fit within a scan line of the raster pattern (as known to persons skilled in the arts). The smaller and fewer in frequency the barcodes, the denser and larger the raster pattern must be. Furthermore, a raster pattern may be achieved by means of rotating/oscillating a linear scanner and/or rotating/oscillating a mirror that reflects the scan line from a linear scanner (as known to those skilled in the arts). If a rotating mirror is used, a geometrically defined prismatic mirror could be used to more accurately control the area that is scanned.

A 2D-Scanner/Imager or QR code scanner (as known to those skilled in the arts) may be used to scan a continuous region along the strip's expected travel path. This scanner can also handle 2D barcodes (as known to those skilled in the arts). This scanner would improve the chances of scanning at least one barcode in a region of space while the strip spans that region. Furthermore, the scanner(s) could be positioned and barcodes arranged (in size, density, and location) so that while the strip spans the scanning region, there will be at least one barcode that can be scanned. The smaller and fewer in frequency the barcodes, the larger the scanning area must be.

The above-mentioned examples could be adapted and modified for barcodes in other orientations. For example, in the case of barcodes parallel/antiparallel to the length of the strip, a single linear scanner's scan line can be oriented parallel/antiparallel to the length strip at some region along the expected travel path of the strip where, as the barcodes pass by, they can be scanned. Furthermore, the barcodes can be arranged (in size, density, and location) so that while the strip spans the scanning region, there will be at least a single barcode in that scanning area (i.e., a barcode can be scanned). The system would then use the information from the scanned barcode(s) to determine the number of doses/packs in the strip. Furthermore, in the case of barcodes parallel/antiparallel to the length of the strip, a pen/wand barcode reader (as known to those skilled in the arts) could also be strategically positioned at some point along the expected travel path of the strip so that the barcodes can be scanned as the strip passes by/through/over the reader.

Barcodes and scanners could principally be used to determine the number of doses/packs remaining in the strip. For example, the user could take doses from the strip and after the user is done, reposition the strip so that the system can reliably scan the barcode(s) on the first dose/pack in the remaining strip. The scanned barcode(s) would convey information to the system about which dose is now the first dose/pack in the remaining strip. Comparing this information to which dose/pack was the original first dose/pack in the strip (before anything was removed from the strip) and/or how many doses/packs in total there were in the complete strip, the system could determine how many doses have been taken and how many remain. Or the dispensing could be controlled (i.e. motorized) so that the system would dispense a certain number of doses or up to a particular dose (i.e. by using the barcodes and scanners to determine how many/which doses were dispensed). After a delay or user input, the system could also retract any leftover doses that were dispensed but not taken. The system could then scan the barcodes on the doses that were retracted (if any) and use this information (i.e. the barcodes could each convey their pack's respective position/dose in the strip) to determine the number of doses/packs remaining in the strip.

Furthermore, the system could be setup so that there is a region of space along the expected travel path of the strip where the leading edge of the strip could be positioned and the system is expected to reliably scan the barcode(s) on the first pack/dose. Using this information the system could then determine the number of doses/packs remaining in the strip. At the outer boundary of the scanning region (the edge furthest from the supply/feed/origin/last dose of the strip, along the expected travel of the strip), a barcode scanner(s) could be strategically positioned (based on the size, location, and frequency of the barcode(s)) to interact with barcodes that are at and/or immediately past this boundary. If the scanner(s) scan a barcode then the system knows that the strip/packs is not within the bounds of the system (i.e. the strip physically extends to/beyond the physical bounds where the system is expected to reliably approximate the number of packs in the strip). The user could then be alerted to reposition the strip back within the bounds of the system or the strip could automatically be repositioned (i.e. by a motor that retracts the strip). This example would require the use of a barcode method that can ensure if the strip spans a scanning region, that a barcode can be scanned from that region. The examples discussed here could be accomplished by using other (or a combination of) tags/indicia discussed herein and the appropriate electrical devices that cooperate with them.

Proximity/Distance Sensors (Electromagnetic, Mechanical, Etc.)

While the total number of doses remaining in the strip can be determined by just using barcodes and a barcode scanner(s), for design reasons such as cost, power, ergonomics, space, aesthetics, flexibility, user friendliness, user freedom, etc. it may be advantageous to utilize a system that detects for the presence and/or absence of the strip/packs without the use of indicia/tags. Electromagnetic waves and mechanical waves, as discussed above, could be used to do this. Specifically, proximity/distance/line/break-beam sensors (as known to those skilled in the arts) could be strategically positioned to detect for the presence of the strip/packs or lack thereof at particular locations. For example, each of the proximity sensors could be positioned to detect a single pack in the strip by aiming each one (as known to those skilled in the arts) at a different position where a pack might be when it is still attached to the strip but where the scanner(s) and assumptions (such as: all doses after the scanned dose(s) are still expected to be attached to the strip) cannot account for it. Multiple proximity sensors could also be used to detect the position of a single pack. A proximity sensor can also be positioned to detect for multiple packs. This can be accomplished by aiming the sensor towards a region of space that multiple packs are expected to occupy. The sensor can then detect the distance of the nearest object/pack and use this information to determine how many packs are in that region (generally the sensor is positioned so that as the detected distance decreases by set intervals, the more packs there are in that region).

Furthermore, the system can use the sensor(s) to detect whether the strip is not within the bounds of the system (i.e. if the strip physically extends to/beyond the physical bounds where the system is expected to reliably determine the number of packs in the strip), by aiming the sensor(s) so that they can detect if the strip is at and/or immediately past the bounds. If there are packs at and/or immediately past this boundary, then the user can be notified to adjust the strip so that it is within the bounds measurable by the system.

Furthermore the system can use the sensor(s) to approximate whether the user is interacting/engaging with the system or not. This may be accomplished by using sensors that are strategically positioned to detect (e.g. through measured reflectance and/or transmittance) objects (i.e. the strip and/or part of a person) in the space where they would most likely only be when the user is interacting/engaging with the system. Conversely, the sensors may be strategically positioned to detect for the absence of objects (e.g., parts of the system) at locations where they would most likely only be absent when the user is interacting/engaging with the system. Motion sensors (e.g., PIR sensor) may also be used to approximate if the system is in use by detecting for motion in the vicinity of the system. The motion sensor would be most effective and least likely to give false positives (i.e. approximating that the system is in use) if it detects for motion in a region where motion is likely only expected when the user is interacting/engaging with the system. Additionally, changes in capacitance, infrared, temperature, inductance, magnetic fields, and other electromagnetic phenomenon may be used to approximate if the system is in use.

Approximating whether the system is in use or not is especially useful for conserving power, extending the longevity of electrical components, and automating the overall process so the user does not have to take an extra step to notify the system that a dose is to be or has been removed from the strip (e.g. by pushing a button). This allows the system to largely remain in a low power state while the user is not interacting/engaging with the system. Once the user begins to use the system it could then exit this low power state and get ready to begin approximating the number of packs remaining (e.g. power up peripherals, check the schedule, check the time, calculate the expected doses, connect to WiFi®, etc.). Once the system automatically determines that the user is done interacting/engaging with the system it could begin to more reliably approximate the number of doses remaining (e.g., by scanning for barcodes, taking data from sensors, and running that information through algorithms) and act on that information (e.g., compare it to the expected number of doses, send out reminders, share the data, provide feedback, etc.). A well designed system should not prematurely assume the user is done interacting/engaging with the system. Such a system would likely falsely approximate the number of remaining packs/doses in the strip and then act on that false information (e.g., provide misleading and/or confusing feedback to the user). Simultaneously, a well-designed system should also approximate the number of remaining packs/doses in the strip and act on that information (e.g., provide feedback to the user) shortly after the user ceases to interact/engage with the system. Such a system may be achieved by the methods disclosed herein. Much of the power saving may also be accomplished through the user consciously providing direct input to the device (e.g., pushing a button, waving a hand over a sensor, etc.) to signal to the system that they are done interacting/engaging with the system; however, it would be at the cost of automation.

It should be noted that the sensors used to detect for the presence and/or movement of objects may be tuned to detect specific types/classes of objects. For example capacitive sensors may be tuned to detect plastics or to detect human flesh at specific locations in/near the system. Or thermal sensors may be used to detect the temperature of objects in/near the system and by comparing different thermal readings (e.g. control readings), the system may be able to infer whether a human is at a specific location in/near the system. This would be useful for when the system is attempting to approximate whether the system is in use or not.

Implementations/Designs

Below are a few possible designs for how the strip, barcodes, a barcode scanner, proximity/distance sensors, and a motion sensor can be combined to create a system that can approximate the number of packs/doses remaining in the strip. The designs may vary depending on several factors, such as the orientation of the strip. The strip is generally oriented vertically so that the doses on the strip are either in ascending (the last dose is at the top of the strip) or descending order (the last dose is at the bottom of the strip). The doses in the strip may also be organized horizontally rather than vertically. The designs described in this document (or its hybrids) may be modified to accommodate directional changes in the strip by repositioning components and/or utilizing and/or modifying other methods/techniques discussed in the present disclosure.

Ascending Strip

With reference to FIG. 17, an exemplary embodiment of the present disclosure depicts a partially opened container 700 that stores and distributes a strip (not shown), similar to the methods described above. As was previously mentioned, the strip (not shown) can be housed in a smaller container (not shown) in a variety of orientations, including being rolled or stacked in a zigzag pattern. The smaller container (not shown) is then placed into container 700 for storage/distribution. Since the strip is ascending, the strip will be placed into the container 700 and exit the slit 705 (slit 705 is created in part by cutout in cover 703 and is visible when cover 703 is closed) in the front face of the container 700 such that when the user interacts/engages with the system as expected, the user will be able to both view the information on the doses/packs in the correct orientation (text is right-side up relative to the user) and access the doses in the correct order (last dose is accessed last). Before the strip exits the slit 705 in the container the strip first would pass over a ramp 702 (such as the one described in another section hereof). The space underneath the ramp 702 may be used to house electronics such as the barcode scanner (not visible) and the ramp confers additional advantages such as those discussed herein. The scanner can be strategically positioned beneath the ramp 702 to scan barcodes on the underside of the strip as they pass over and/or rest on top of the ramp 702. The scanner can accomplish this through the means discussed in this document. A portion of or the entire ramp 702 can be made to allow the scanner to scan the barcodes, by controlling the material of the ramp (e.g. using transparent materials) and/or strategically removing material from the ramp 702.

Figure 22:
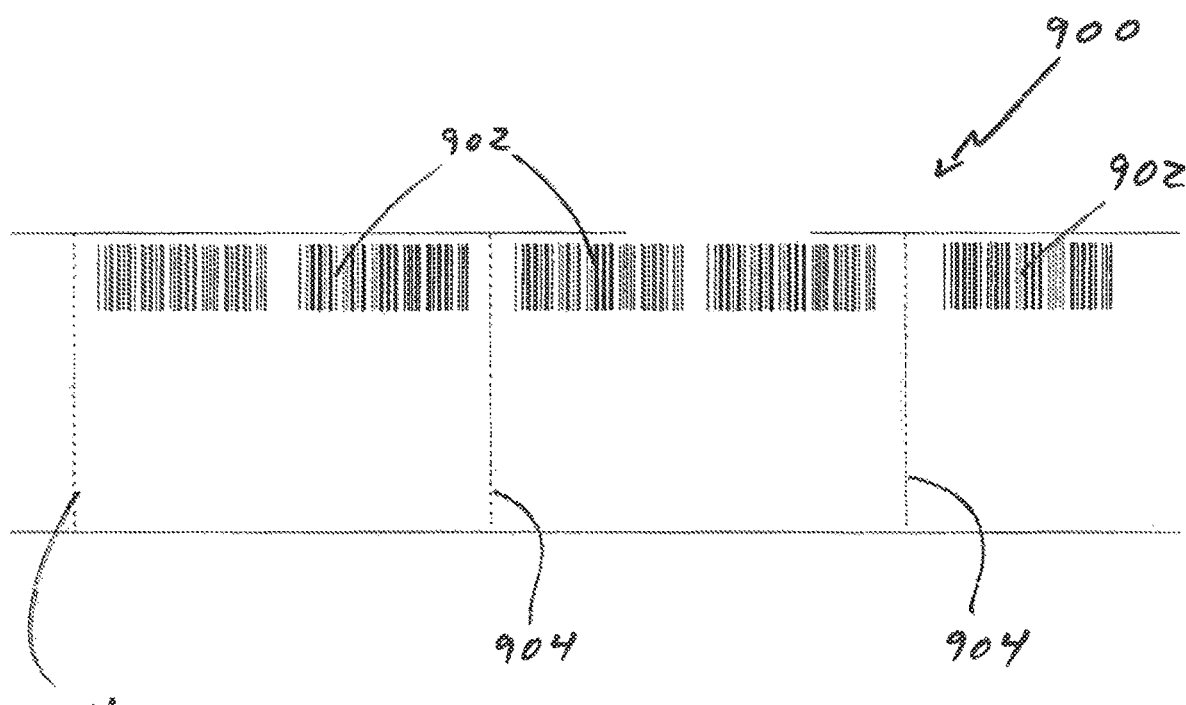
FIG. 22 is a schematic illustration of a series of barcodes on a small piece of strip packaging according to an exemplary embodiment of the present disclosure.

In this embodiment, the barcodes will be on the underside of the strip, parallel to the length of the strip, equally spaced from the sides of the strip, and the same position on each pack (refer to strip 900 in FIG. 22 with barcodes 902 and perforation lines 904). A linear barcode scanner will be strategically positioned beneath the ramp 702 so that its scan line will be parallel to the length of the strip and can scan the barcodes as they pass over the ramp 702. The section of the ramp 702 that the barcodes pass over will be made of a transparent plastic that allows the scanner to scan the barcode(s) through the ramp 702. The barcodes will be strategically positioned so that while the strip spans the scanning region, there will be at least one barcode in the scanner's scanning region. This positioning will depend on the length of the ramp 702, the length of the scan line, the length of the packs, and length of the barcodes. For this design, the length of the ramp 702 will be slightly greater than the length of one pack, the scan line will extend over the entire length of the ramp, the barcode lengths will be about a third the length of the packs, and there will be two barcodes on each pack.

Each of the barcodes will contain a unique numerical value that corresponds to a specific position along the strip and ergo a specific dose. When the scanner scans the barcode(s), that information along with some assumptions about the nature of the system (such as: if one barcode on a pack is scanned then it means the entire pack must be present) can be used to determine which dose(s) are on top of the ramp 702 and being scanned by the scanner. Then, using the assumption that all the doses after the dose(s) that have been scanned are still attached to the strip, the system can determine how many doses/packs are still attached to the strip up to the scanner (i.e., still in the container). This system alone, however, would be unable to account for any doses still attached to the strip but before the scanned dose(s). These packs would be hanging outside, in front of the front face 706 of the container 700. These packs still attached to the strip but that the scanner and assumptions cannot account for will be referred to as additional packs.

To account for these additional packs, this design will utilize infrared proximity/distance sensors (not shown) strategically positioned in/behind the front face 706 of the container 700 and beneath the ramp 702, to detect for additional packs. These infrared proximity/distance sensors will be positioned to detect for obstacles/objects (as known to those skilled in the arts) at/near the front face of the container, these obstacles/objects will likely be the additional packs in front of the front face 706 of the container 700. The spacing/positioning of these sensors in/behind the front face 706 of the container 700 will depend on the size of the packs, the range that the barcode scanner and assumptions can account for, and the information that is derived from the scanned barcodes and assumptions about the nature of the system.

For this design, two groups of sensors will be used to detect for each possible additional pack. The first group of sensors used to detect for each additional pack will be referred to as the $1/3$ sensors and second will be referred to as the $2/3$ sensors. The first $1/3$ sensor will be positioned $1/3$ the length of a pack/dose from the outer border of the scanning region along the expected travel path of the strip. In this design, that means $1/3$ the length of a pack/dose down the front face 706 of the container 700 from the slit/opening 705 in the container 700 (which the ramp and ergo the scanning region are flush with). The first $2/3$ sensor will be positioned $2/3$ the length of a pack/dose from the outer border of the scanning region along the expected travel path of the strip. In this design, that means $2/3$ the length of a pack/dose down the front face 706 of the container 700 from the slit/opening 705 in the container 706. The first $1/3$ and $2/3$ sensors will be used to detect for the first possible additional pack. Each subsequent $1/3$ sensor will be placed a full pack length from the previous $1/3$ sensor and be used to detect the next possible additional pack. Each subsequent $2/3$ sensor will be placed a full pack length from the previous $2/3$ sensor and also be used to detect the next possible additional pack.

When this setup is combined with the information from the barcodes and the assumptions about the nature of the system, the system can approximate the number of additional doses/packs. For this design, while the strip spans the scanning region there will always be one or two barcodes being scanned. If both barcodes from the same pack are scanned, the system assumes that entire pack is spanning the scanning region, so the system assumes the additional pack closest to the slit 705 has its trailing edge (the one that while traveling along the strip is closest to the last dose) at/near the slit 705 in the container 700. Therefore, the number of $2/3$ sensors that are "triggered" should be the number of additional packs that the information from the scanner and assumptions alone cannot account for. The barcodes will also be positioned so that during this scenario no $1/3$ sensors should be "triggered" without their partner $2/3$ sensor being "triggered."

If one barcode is scanned and it is the one closest to the trailing edge of the pack (patterns and/or unique numbers in the barcodes will allow the system to identify whether the barcode is from the leading or trailing edge of the pack), the system assumes that a small portion of the pack it is scanning must be hanging out of the slit. The barcodes will be strategically positioned so the amount that the pack can stick out of the slit during this scenario should not cause the "trigger" of the $2/3$ sensor of the next possible additional pack (relative to if both barcodes on the scanned pack were in the scanning region). Therefore, the number of $2/3$ sensors that are "triggered" should be the number of additional packs that the information from the scanner and assumptions alone cannot account for. If two barcodes are scanned, each from a different pack (i.e., the barcode nearest the trailing edge of one pack and the barcode nearest the leading edge of another), the system assumes that a larger portion of the pack, whose trailing edge barcode was scanned, should be hanging out of the slit 705. The barcodes will be strategically placed so that during this scenario, the $1/3$ sensor of the next possible additional pack (relative to if both barcodes of the pack whose trailing edge barcode is being scanned, were in the scanning region) should be "triggered" and so that the $2/3$ sensor of the next possible additional pack (relative to if both barcodes, of the pack whose trailing edge barcode is being scanned, were in the scanning region) may be "triggered." The number of $2/3$ sensors that are "triggered" should be the number of additional packs that information from the barcode scanner and assumptions cannot account for, unless the last sensor (the sensor furthest from the last dose along the expected travel path of the strip) that is "triggered" is not a $1/3$ sensor: in this case the number of additional packs would be the number of "triggered" $2/3$ sensors minus one. If one barcode is scanned and it is the one closest to the leading edge of the pack the system assumes that most of the dose before the one it is scanning may be hanging out of the slit 705. The barcodes will be positioned so that in this scenario, the number of $2/3$ sensors that are "triggered" should be the number of additional packs that the information from the barcode scanner and assumptions cannot account for, unless the last sensor (the sensor furthest from the last dose along the expected travel path of the strip) that is "triggered" is a $1/3$ sensor: in this case the number of additional packs would be the number of $2/3$ sensors plus one.

It should be noted that if a sensor used to detect additional packs is "triggered" but any of the sensors used to detect additional packs positioned before it (in this example that means closer to the slit 705) are not "triggered," the system assumes an error has occurred and notifies the user. For this design, the sensors will be strategically positioned to detect up to one additional pack immediately outside of what the scanner and assumptions can account for. Other sensor(s) will be added to the system, to approximate if the strip extends beyond the physical bounds of where the system (e.g. information from barcodes/scanner, sensors, and assumptions) can reliably approximate the number of doses in the strip. Specifically, an IR proximity/distance sensor will be placed near or at the edge of the outer bound (the bound furthest along the expected travel path of the strip) where the leading edge of the strip can be positioned and have the system reliably approximate the number of remaining doses/packs. When this sensor is "triggered" (i.e. it detects the strip), the user will be notified to readjust the strip, in this case so that there is no more than one pack hanging outside of the container 700. In another embodiment of this design, a single sensor could be used to detect for each additional pack, and they could be positioned so that the sensor for each subsequent additional pack is placed closer to the previous sensor.

In this design, approximating whether the user is interacting/engaging with the system will be accomplished through the use of an infrared distance/proximity sensor (not shown), a passive infrared (PIR) sensor (not shown), and delays/timers. In this design, the PIR sensor will be strategically positioned at the bottom of the container on a base 708 that extends from the front face 706 of the container 700. The PIR sensor will be positioned and housed so that a confined space is "visible" (as known to those skilled in the arts) to the sensor. In this design, that space will be the front face 706 of the container 700 (from the base 708 to the slit 705 and up to the top of the container 700) and 1-3 inches in front of it. With this "view", movement will most likely only be detected when the user is interacting/engaging with the system and come from the movement of the strip and/or the user (if the user is using the system as expected). So, whenever the PIR sensor detects movement the system will assume that that the user is using the system. This is very useful for approximating when the user initially begins to use the system, but in this design, it is limited when approximating whether the user is still using the system, since it must detect movement at/near the front face of the container and that may not be occurring during use after the initial interaction/engagement. For this reason, an infrared distance sensor will be used to assist in approximating whether the system is still in use after the initial interaction/engagement. The sensor will also be positioned on the base 708 in front of the front face 706 of the container 700. Rather than being aimed at the face 706 of the container 700 and detecting motion, however, this sensor will be aimed upwards and detect for obstacles/objects above the base 708 of the container 700. In this example the sensor will be placed far enough from the face 706 so that one or two packs hanging out of the slit 705 will not "trigger" the sensor. To improve the chances that it can approximate for interaction/engagement with the system when the PIR sensor cannot, the sensor would be placed closer to the front face 706 of the container 700 than the PIR sensor. The sensor will be placed so that the system can assume that there should be no obstacles/objects directly above the position of the sensor up to about the height of the container, while the user is not interacting/engaging with the system. The sensor is able to assume this in part because of the following: the distance of the sensor from the front face (preventing a false "trigger" from packs hanging out of the slit 705, as described above), the IR sensor in the front face 705 that notifies the user when the strip extends beyond the bounds where the system can reliably function (this prevents the strip from piling on top of the base 708 and covering sensor and creating a false "trigger"), and the negative space created in front of the front face 706 of the container 700 over the extended base 708 (if used as expected, it is unlikely that the user will place an object in this space). Therefore, when the sensor detects an obstacle/object directly above it (and above the base 708) up to about the height of the container 700, that obstacle/object will most likely have been positioned there because the user is interacting/engaging with the system and that obstacle/object will most likely be the strip or the user (e.g. the user pulls the strip towards them self and the strip is hanging above the base and "triggering" the sensor, or their hand is touching the strip at the front face 706 and their hand is "triggering" the sensor). Furthermore, since these are approximations and the user may not be properly using the system at every moment, delays/timers will also be incorporated into the code so that the system can detect for possible interaction/engagement over a period of time, thereby reducing the chances of the system prematurely assuming the user is done interacting/engaging the with the system. If the system approximates that the user has been engaging/interacting with the system for a lengthy period of time (i.e. a time significantly longer than it takes to remove a dose), it will assume an error has occurred and notify the user.

This example may also contain a child resistant cover/door as discussed herein. For this example, it may be advantageous for the cover to be transparent to IR so as not to interfere with the IR sensors.

Alternative Embodiment

In an alternative embodiment, the barcodes could be perpendicular to the length of the strip and placed on the front face of the strip. In this embodiment, a different setup for the barcode scanner would need to be used. With reference to FIG. 18, the ramp 752 has been altered so that at its apex a flat platform 754 extends into the container 750. The strip of medication would have to pass over this platform 754 before going over the ramp 752 and exiting the container 700 out of the slit 758 (slit 758 is created by cutout in lid 756 and is visible when lid 756 is closed). In one version, a 2D barcode scanner (not visible) can be strategically positioned in the lid 756 of the container 750 so that it can scan a region over the platform 754. The scanner can then scan the front face of the strip for barcodes, as the strip passes over or is resting on the platform 754. The scanner(s) could be positioned and barcodes arranged (in size, density, and location) so that while the strip spans the scanning region, there will be at least one barcode that can be scanned. In an alternative version, a linear barcode scanner could be used instead and strategically positioned in the lid 756 so that the scan line is aimed at a rotating mirror (not shown). The mirror can reflect the scan line in a manner that orients it parallel to the barcodes and moves it along the platform 754 in a direction perpendicular to the barcodes. This could be accomplished by, for example, placing the linear scanner in the lid 756 so that the scanner is parallel to the top face of the lid 756 and the scan line is parallel to the width of the container 750. Above the apex of the ramp 752 there could be a prismatic mirror (not shown) that reflects the scan line down towards the platform 754 and as the prism rotates, the scan line would move away from the mirror towards the back of the container 750 and along the platform 754 where it would scan any barcodes on the platform 754. This process would repeat as the prism rotates (the mirror could be connected to a motor that rotates it at a set speed). The scanning region size and barcode size, frequency, and positioning can be controlled so that while the strip spans the scanning region there will be at least one barcode that can be scanned by the system. Combining this system with the assumption that all doses after the scanned dose(s) are still attached to the strip, the system could then use IR sensors (not shown) to approximate the presence of packs still attached to the strip that the scanner(s) and assumption(s) cannot account for (referred to as additional packs). This would include having IR sensors detect for the presence of possible additional packs inside the container. Or, the assumptions may be modified so that the system not only assumes all doses after the scanned dose(s) are still attached to the strip but also assumes that all doses before the scanned dose(s) up to the slit 758 in the container 750 are still attached to the strip (which would be a fixed number of packs/doses). This way, IR sensors would only be needed to detect for the presence of additional packs outside the container 750. This system would also be combined with the methods described above that are used to approximate whether the user is interacting/engaging with the system.

Alterations/combinations of methods discussed in this document could also be used to ensure that the system can reliably approximate the number of additional packs.

Descending Strip

Figure 19:
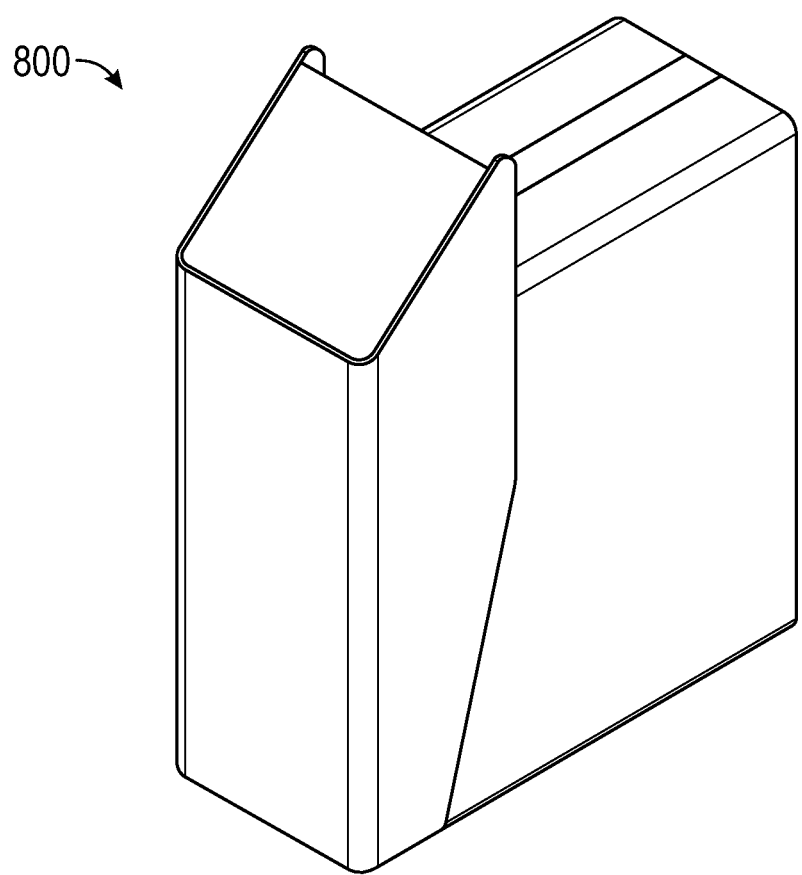
FIG. 19 depicts a perspective view of an alternate embodiment of a closed big box that provides indicia-reading capabilities of a descending strip, according to the present disclosure.
Figure 20:
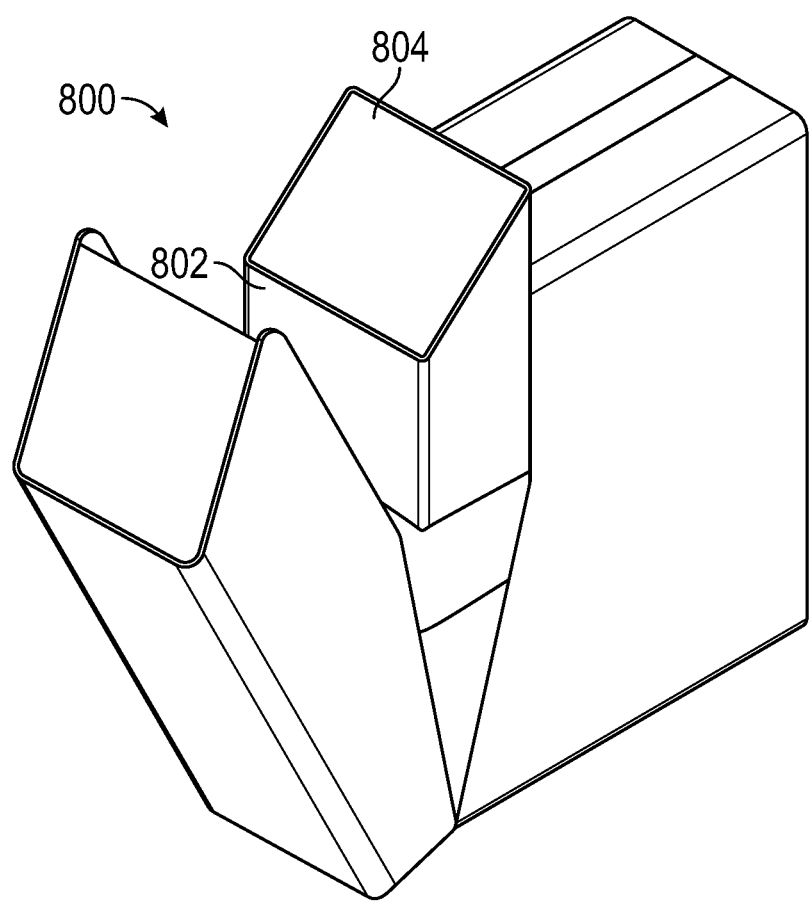
FIG. 20 depicts a perspective view of an alternate embodiment of a partially opened big box that provides indicia-reading capabilities of a descending strip, according to the present disclosure.

With reference to FIGS. 19 and 20, container 800 uses a descending strip rather than an ascending strip. The strip (not shown) could be placed into a container where the strip would first have to travel over a platform 802 and then over a ramp 804 to exit the container 800. If the barcodes were parallel to the length of the strip and on the underside of the strip (like in FIG. 17), the barcode scanner (not visible) could be strategically positioned beneath the platform 802 to scan the barcodes as they passed over/rested on the platform 802 (like in FIG. 17). If the barcodes were on the front face of the strip and perpendicular to the length of the strip (like in FIG. 18), the scanner could be strategically positioned in the container 800 to scan the barcodes as they passed over/rested on the platform 802 (like in FIG. 18 where the scanner was placed in the lid of the container). Infrared proximity/distance sensors (not shown) could then be strategically positioned to account for additional packs (the packs the scanner and assumptions can't account for). The system could also use proximity/distance and motion sensors to approximate whether the system is in use (like in FIGS. 17 and 18).

Alternative Designs for Big Box

Figure 21:
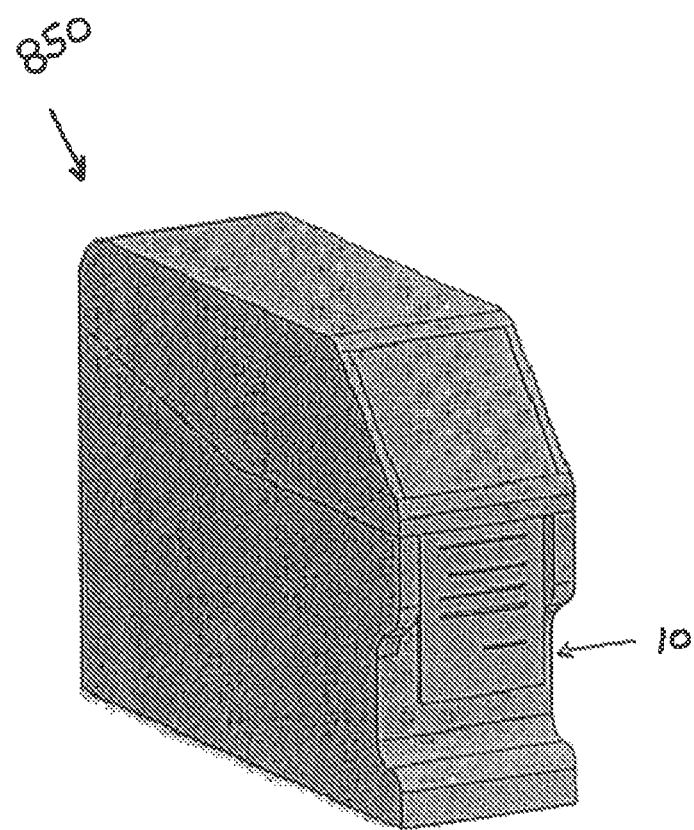
FIG. 21 depicts a perspective view of an alternate embodiment of the big box that substantially encapsulates the strip packaging, according to the present disclosure.

With reference to FIG. 21, the strip 10 can remain within the confines of the big box 850 once it exits the slit, making the strip hanging out of the slit feel like part of the entire system rather than a protrusion. This would also allow for the child resistant covering to be more streamlined with the design of the container.

With reference to FIG. 16, an alternate embodiment of big box 600 is one way to enable the above mentioned example. The user would open the side door 602 to the container 600 (potentially child-resistant) and place a rolled up strip into the container. The user would then feed the strip (not shown) through the gap 604 that extends from the interior of the container to the exterior front face of the container. The user would close the door 602 to the container 600. The strip (not shown) could have unique barcodes associated with each dose/pack on the strip and by extension, a specific location on the strip. A barcode reader could then be strategically positioned to scan through the window labeled by arrow A. At this point, the packs in the gap 604 are kept near the window 606 so that the barcodes on them can be easily and consistently read through the window. The strip (not shown) can be kept taut and in place by positioning flexible elastic material(s) ("stoppers") in the gap 604 that extends from the interior of the container. The material(s) would be positioned at an angle oriented with the direction of travel of the strip out of the container 600 and would be adhered to only one side of the gap 604. This would allow the strip (not shown) to be easily pulled out of the container 600 but hinder the strip from falling back into the container. This would also keep the sections in between theses "stoppers" firm and taught which can be used to keep the region that is to be scanned firm and taught. IR proximity sensors could be placed on the front face of the container 600 to check for the presence of additional packs that are hanging out past the slit 608. Or a single IR sensor could be placed on the bottom front foot of the device that would check how far the nearest pack is from the sensor (the closer the nearest pack, the more packs that are hanging out).

If too many packs/doses are hanging out past the slit 608, the sensor(s) would not be able to reliably determine how many additional packs are hanging out. To accommodate for this, a threshold level may be set so that if the user has a certain number of packs or greater number of packs hanging out, they will be instructed to reinsert the strip and to follow proper loading and user directions (e.g., max number of packs/doses that can hang out).

The slit where the strip emerges from the front face can be made child-resistant in a manner similar to those discussed herein. The system could also use sensors to approximate whether the system is being used or not.

According to the present disclosure, exemplary embodiments and implementations of systems and methods for storing, monitoring and dispensing medications have been described. However, it is to be understood that the disclosed embodiments/implementations are illustrative of the disclosed systems and methods. The present disclosure is neither limited by or to the exemplary embodiments/implementations described herein. Rather, the present disclosure extends to and encompasses variations, modifications, refinements and improvements to the disclosed systems/methods, as will be apparent to persons skilled in the art based on the disclosure herein. Moreover, "hybrid" implementations of the disclosed features/functions are expressly contemplated according to the present disclosure, i.e., embodiments/implementations that use features/functions (in whole or in part) of a first disclosed embodiment in combination with features/functions (in whole or in part) of a second disclosed embodiment (and potentially a third embodiment, a fourth embodiment, and so on).

The invention claimed is:

1. A system for delivering medications, comprising:
   a. a first box configured and dimensioned to receive a strip of pouches containing one or more medications;
   b. a strip of pouches positioned in the first box, the strip including readable means for determining that a pouch has been disengaged from the strip, advanced relative to a reference position, or a combination of the foregoing;
   wherein the first box defines an opening or slit at a top surface thereof;
   wherein a portion of the strip extends through the opening or slit and is detachably secured with respect to the top surface of the box.

2. A system according to claim 1, further comprising (i) indicia associated with the strip, and (ii) a device or system for reading the indicia to monitor or determine position or status of the strip.

3. A system according to claim 1, wherein the readable means is readable based on interaction with a light source, a motorized feed system or a tag system.

4. A system according to claim 1, further comprising a trigger mechanism that interacts with the strip to determine information associated with the strip.

5. A system according to claim 1, wherein the readable means includes electronic elements mounted or otherwise applied to the strip.

6. A system according to claim 5, wherein the electronic elements includes a first strip of conductive material along a first edge of the strip, a second conductive material along a second edge of the strip, and a cross-element associated with each pouch that extends between the first and the second strips.

7. A system according to claim 1, further comprising a second box configured and dimensioned to receive the first box.

8. A system according to claim 7, wherein the second box includes a ramp that extends upward from a top face thereof.

9. A system according to claim 7, further comprising a door movably mounted with respect to a front face of the second box.

10. A system according to claim 7, wherein the second box includes electrical contacts in a base thereof, the electrical contacts in the second box configured and dimensioned to electrically communicate with electrical contacts formed in the base of the first box.

11. A system according to claim 7, wherein the second box includes circuitry that is adapted to measure or monitor information related to a strip positioned in the first box positioned therewithin.

12. A system according to claim 11, further comprising communication functionality in communication with the circuitry for communicating information to a patient or other entity.

13. A system according to claim 7, wherein the front face of the second box includes one or more sensors to detect for additional packs.

14. A system according to claim 13, wherein the sensors are selected from the group consisting of infrared proximity or distance sensors, and motion sensors for detecting user movement.

15. A system for delivering medications, comprising:
a. a first box configured and dimensioned to receive a strip of pouches containing one or more medications;
b. a strip of pouches including readable means for determining that a pouch has been disengaged from the strip and/or advanced relative to a reference position;
wherein once a pouch has been removed from the strip, an electrical measurement of the circuitry of the strip decreases in a predictable manner;
wherein the reduction of the electrical measurement can be used to calculate the total number of pouches remaining on the strip and the total number of pouches removed from the strip.

16. The system according to claim 15, wherein the predictable electrical measurement is the capacitance of the circuitry of the strip.

17. The system according to claim 15, wherein the predictable electrical measurement is the resistance of the circuitry of the strip.

18. A system for dispensing a strip of pouches, comprising:
a. a first box configured and dimensioned to receive a strip of pouches containing one or more medications;
b. a second box configured and dimensioned to receive the first box, said second box defining a ramp;
wherein indicia is located on or in the strip of pouches;
wherein a travel path is defined for the strip that extends upward to an apex of the ramp and then downward along a front face of the second box;
wherein the second box includes means of "reading" the indicia located on or in the strip; and
wherein the front face of the second box includes one or more sensors to detect additional packets, user movement or both additional packets and user movement.

19. A system according to claim 18, wherein the sensors are infrared proximity or distance sensors.

20. A system according to claim 18, further comprising one or more mirrors associated with the second box, said mirrors being adapted to assist a processor associated with the second box in "reading" the indicia on the strip.

* * * * *